United States Patent
Helentjaris et al.

(10) Patent No.: US 6,713,666 B2
(45) Date of Patent: Mar. 30, 2004

(54) INVERTASE INHIBITORS AND METHODS OF USE

(75) Inventors: Timothy G. Helentjaris, Ankeny, IA (US); Nicholas J. Bate, Urbandale, IA (US); Stephen M. Allen, Wilmington, DE (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 25 days.

(21) Appl. No.: 09/780,717

(22) Filed: Feb. 9, 2001

(65) Prior Publication Data

US 2001/0044941 A1 Nov. 22, 2001

Related U.S. Application Data

(60) Provisional application No. 60/181,509, filed on Feb. 10, 2000.

(51) Int. Cl.$^7$ .............................. A01H 5/00; A01H 5/10; C12N 15/63; C12N 15/82

(52) U.S. Cl. .................... 800/320.1; 800/278; 800/298; 435/320.1; 435/419; 536/23.2; 536/24.5

(58) Field of Search ................................ 800/278, 284, 800/286, 288, 298, 317.3, 320.1; 536/23.1, 23.2, 23.6, 24.5, 23.74; 435/201, 320.1, 419

(56) References Cited

U.S. PATENT DOCUMENTS 5,962,764 A   10/1999   Briggs et al.

FOREIGN PATENT DOCUMENTS

| DE | WO 00/09719 A1 * | 2/2000 | ........... C12N/15/82 |
|---|---|---|---|
| WO | WO 98/04722 A1 | 2/1998 | |
| WO | WO 98/04722 | 2/1998 | |
| WO | WO 00/09719 A1 | 2/2000 | |
| WO | WO 00/09719 | 2/2000 | |

OTHER PUBLICATIONS

Sander A. et al., FEBS Letters 385, 1996, pp. 171–175.*
Schaewen A. et al., The EMBO Journal 1990, vol. 9, No. 10, pp. 3033–3044.*
Weber H. et al., The Plant Journal 1998, 16(2) pp. 163–172.*
Bussis D. et al., Planta 1997, 202:126–136.*
Bussis D. et al., Planta 1997, 202:126–136.*
Greiner S. et al. Plant Physiology, 1998, vol. 116, pp. 733–742.*
Gordon–Kamm W. et al. The Plant Cell, Jul. 1990, vol. 2, pp. 603–618.*
Bussis et al. "Solute accumulation and decreased photosynthesis in leaves of potato plants expressing yeast–derived invertase either in the apoplast, vacuole or cytosol", *Planta* (1997) 126–136, vol. 202.

Cheng, et al., "The Miniature1 Seed Locus of Maize Encodes a Cell Wall Invertase Required for Normal Development of Endosperm and Maternal Cells in the Pedicel", The Plant Cell, 971–983.

Greiner, et al., Cloning of a Tobacco Apoplasmic Invertase Inhibitor, *Plant Phsiol.*, (1998) 733–742, vol. 116.

Greiner, et al., "Ectopic expression of a tobacco invertase inhibitor homolog prevents cold–induced sweetening of potato tubers", *Nature Biotechnology*, (1999) 708–711, vol. 17.

Taliercio, et al., "Isolation, Characterization and Expression Analyses of Two Cell Wall Invertase Genes in Maize", *Journal of Plant Physiology*, (1999), 197–204.

Weil, et al., "A 17–kDa *Nicotiana tabacum* cell–wall peptide acts as an in–vitro inhibitor of the cell–wall isoform of acid invertase", *Planta*, 1994, 438–445, vol. 193.

Zinselmeier, et al., "Low Water Potential Disrupts Carbohydrate Metabolism in Maize (*Zea mays* L.) Ovaries", *Plant Physiology*, 1995, 385–391, vol. 107.

Zinselmeier, et al, "Reversing Drought–Induced Losses in Grain Yield: Sucrose Maintains Embryo Growth in Maize". *Crop Science*, 1995, 1390–1400, vol. 35.

Zinselmeier, et al, "Starch and the Control of Kernel Number in Maize at Low Water Potentials", *Plant Physiology*, 1999, 25–35, vol. 121.

Sander, A., et al., "Sucrose Protects Cell Wall Invertase But Not Vacuolar Invertase Against Proteinaceous Inhibitors", *FEBS Letters*, 1996, pp. 171–175, vol. 385.

Von Schaewen, A., et al., "Expression of a Yeast–Derived Invertase in the Cell Wall of Tobacco and Arabidopsis Plants Leads to Accumulation of Carbohydrate and Inhibition of Photosynthesis and Strongly Influences Growth and Phenotype of Transgenic Tobacco Plants", *The EMBO Journal*, 1990, pp. 3033–3044, vol. 9, No. 10.

(List continued on next page.)

*Primary Examiner*—David T. Fox
*Assistant Examiner*—Russell Kallis
(74) *Attorney, Agent, or Firm*—Alston & Bird LLP

(57) ABSTRACT

Methods and compositions for increasing yield in plants, particularly seed plants, are provided. The compositions comprise novel nucleic acid molecules encoding invertase inhibitors, antisense nucleotides corresponding to invertase inhibitors, and variants and fragments thereof. Such compositions find use in methods to modulate invertase activity in plants. The compositions are also useful in methods to modulate kernel development and for protecting plants against the harmful/detrimental effects of stress and adverse environmental conditions. The nucleotide sequences may be provided in constructs for temporal, developmental, and tissue preference.

Transformed plants, plant cells, tissues, and seeds are additionally provided.

19 Claims, 4 Drawing Sheets

OTHER PUBLICATIONS

Weber, et al. "Expression of a Yeast–Derived Invertase in Developing Cotyledons of *Vicia Narbonensis* Alters the Carbohydrate State and Affects Storage Functions", *The Plant Journal*, 1998, pp. 163–172, vol. 16, No. 2.

Russell, P., Invertase Inhibitor in Tomato Fruit, Phytochemistry, 1994, vol. 36(3) pp. 543–546.

EMBL Database Accession No. AU030354, 1998.

Pressey, R., "Invertase Inhibitor in Tomato Fruit," *Phytochemistry*, 1994, pp. 543–546, vol. 36(3), Elsevier Science Ltd., Great Britain.

EMBL Database Report for Accession No. AU030354, Oct. 16, 1998 (XP–002173419).

EMBL Database Report for Accession No. AW147128, Nov. 4, 1999 (XP–002180853).

EMBL Database Report for Accession No. C93615, Apr. 28, 1998 (XP–002180854).

EMBL Database Report for Accession No. BE360882., Jul. 28, 2000 (XP–002180855).

EMBL Database Report for Accession No. BF729260, Jan. 11, 2001 (XP–002180856).

\* cited by examiner

SEQUENCE LISTING

<160> NUMBER OF SEQ ID NOS: 54

<210> SEQ ID NO 1
<211> LENGTH: 665
<212> TYPE: DNA
<213> ORGANISM: Zea mays
<220> FEATURE:
<221> NAME/KEY: CDS
<222> LOCATION: (68)...(598)

<400> SEQUENCE: 1

```
gtcgacccac gcgtccggca catttgaatt tggatttgca ttgtcagtca ggccagtcaa        60 ggggacc atg aag ctt ctg caa gct ctg tgc cct ctc gtc atc ctc ctc       109
        Met Lys Leu Leu Gln Ala Leu Cys Pro Leu Val Ile Leu Leu
        1               5                   10 gcc tgc tcc acg tcc aac gct tcc gtc cta caa gac gcg tgc aag tcc       157
Ala Cys Ser Thr Ser Asn Ala Ser Val Leu Gln Asp Ala Cys Lys Ser
 15                  20                  25                  30 ttc gcc gct aag atc ccg gac acc ggc tac gcc tac tgc atc aag ttc       205
Phe Ala Ala Lys Ile Pro Asp Thr Gly Tyr Ala Tyr Cys Ile Lys Phe
                 35                  40                  45 ttc cag gcc gac agg gga agc gcc ggc gcg gac aag cgt ggc ctc gcc       253
Phe Gln Ala Asp Arg Gly Ser Ala Gly Ala Asp Lys Arg Gly Leu Ala
             50                  55                  60
```

-continued

| | |
|---|---|
| gcc atc gcc gtg agg atc atg ggg gca gcc gcc aag agc acc gcc agt<br>Ala Ile Ala Val Arg Ile Met Gly Ala Ala Ala Lys Ser Thr Ala Ser<br>65                          70                      75 | 301 |
| cac atc gcc gcc ctg cgg gcc tcc gag aag gac aag gag cgg ctg gcg<br>His Ile Ala Ala Leu Arg Ala Ser Glu Lys Asp Lys Glu Arg Leu Ala<br>    80                       85                     90 | 349 |
| tgc ctc agc gat tgc tcc gag gtg tac gcg cag gcc gtg gac cag acc<br>Cys Leu Ser Asp Cys Ser Glu Val Tyr Ala Gln Ala Val Asp Gln Thr<br>95                      100               105             110 | 397 |
| ggc gtg gcg gcg aag ggc atc gcc tcg ggc acg ccc cgg ggc cgc gcg<br>Gly Val Ala Ala Lys Gly Ile Ala Ser Gly Thr Pro Arg Gly Arg Ala<br>               115              120              125 | 445 |
| gac gcg gtg atg gcg ctc agc acg gtg gag gat gcc ccc ggc acc tgt<br>Asp Ala Val Met Ala Leu Ser Thr Val Glu Asp Ala Pro Gly Thr Cys<br>         130               135             140 | 493 |
| gag cag ggg ttc cag gac ctg agc gtg cgt tcg ccg ctg gcc tcg gag<br>Glu Gln Gly Phe Gln Asp Leu Ser Val Arg Ser Pro Leu Ala Ser Glu<br>        145                150             155 | 541 |
| gac gcc ggg ttc cgg aag gat gcg tcc atc gcg ctg tct gta acg gcc<br>Asp Ala Gly Phe Arg Lys Asp Ala Ser Ile Ala Leu Ser Val Thr Ala<br>160                       165              170 | 589 |
| gcg ttg taa gcaaaggtgt ataatccttt tcgatatagg ttaaaaatga<br>Ala Leu *<br>175 | 638 |
| ataaaaaaaa aaaaaaaggg cggccgc | 665 |

<210> SEQ ID NO 2
<211> LENGTH: 176
<212> TYPE: PRT
<213> ORGANISM: Zea mays

<400> SEQUENCE: 2

Met Lys Leu Leu Gln Ala Leu Cys Pro Leu Val Ile Leu Leu Ala Cys
1                  5                 10               15

Ser Thr Ser Asn Ala Ser Val Leu Gln Asp Ala Cys Lys Ser Phe Ala
             20                 25               30

Ala Lys Ile Pro Asp Thr Gly Tyr Ala Tyr Cys Ile Lys Phe Phe Gln
                35                 40              45

Ala Asp Arg Gly Ser Ala Gly Ala Asp Lys Arg Gly Leu Ala Ala Ile
50                  55                 60

Ala Val Arg Ile Met Gly Ala Ala Ala Lys Ser Thr Ala Ser His Ile
65                  70                 75               80

Ala Ala Leu Arg Ala Ser Glu Lys Asp Lys Glu Arg Leu Ala Cys Leu
             85                 90               95

Ser Asp Cys Ser Glu Val Tyr Ala Gln Ala Val Asp Gln Thr Gly Val
                100             105             110

Ala Ala Lys Gly Ile Ala Ser Gly Thr Pro Arg Gly Arg Ala Asp Ala
             115              120             125

Val Met Ala Leu Ser Thr Val Glu Asp Ala Pro Gly Thr Cys Glu Gln
       130               135             140

Gly Phe Gln Asp Leu Ser Val Arg Ser Pro Leu Ala Ser Glu Asp Ala
145                150             155             160

Gly Phe Arg Lys Asp Ala Ser Ile Ala Leu Ser Val Thr Ala Ala Leu
                165             170            175

<210> SEQ ID NO 3
<211> LENGTH: 531

-continued

```
<212> TYPE: DNA
<213> ORGANISM: Zea mays

<400> SEQUENCE: 3
atgaagcttc tgcaagctct gtgccctctc gtcatcctcc tcgcctgctc cacgtccaac     60
gcttccgtcc tacaagacgc gtgcaagtcc ttcgccgcta agatcccgga caccggctac    120
gcctactgca tcaagttctt ccaggccgac aggggaagcg ccggcgcgga caagcgtggc    180
ctcgccgcca tcgccgtgag gatcatgggg gcagccgcca agagcaccgc cagtcacatc    240
gccgccctgc gggcctccga aaggacaag gagcggctgg cgtgcctcag cgattgctcc     300
gaggtgtacg cgcaggccgt ggaccagacc ggcgtggcgg cgaagggcat cgcctcgggc    360
acgccccggg gccgcgcgga cgcggtgatg gcgctcagca cggtggagga tgcccccggc    420
acctgtgagc aggggttcca ggacctgagc gtgcgttcgc cgctggcctc ggaggacgcc    480
gggttccgga aggatgcgtc catcgcgctg tctgtaacgg ccgcgttgta a              531

<210> SEQ ID NO 4
<211> LENGTH: 981
<212> TYPE: DNA
<213> ORGANISM: Zea mays
<220> FEATURE:
<221> NAME/KEY: CDS
<222> LOCATION: (58)...(723)

<400> SEQUENCE: 4
gaattcggca cgagcatcgt ccacacaaac acatcctact ctctttagca aaaagac atg    60
                                                                Met
                                                                  1 gca acc acc aag agg gag aag gtc atc ctc gtc ctg ctg ttc tcc ctg      108
Ala Thr Thr Lys Arg Glu Lys Val Ile Leu Val Leu Leu Phe Ser Leu
             5                  10                  15 acg atg ctc cct ctc agc acc ctc ggc acc cgc tcc ggc ccg gcg gcc      156
Thr Met Leu Pro Leu Ser Thr Leu Gly Thr Arg Ser Gly Pro Ala Ala
         20                  25                  30 gtg cag cac cac ggc cac ggc ggc acc acc aag cac ccc tcg cct cct      204
Val Gln His His Gly His Gly Gly Thr Thr Lys His Pro Ser Pro Pro
     35                  40                  45 tca cca gcc acg gcg gcg ctg gta cgc agc acg tgt aac tcc acg gcg      252
Ser Pro Ala Thr Ala Ala Leu Val Arg Ser Thr Cys Asn Ser Thr Ala
 50                  55                  60                  65 tac tac gac gtg tgc gtg tcc gcg ctg ggc gcc gac ccg tcc agc gcc      300
Tyr Tyr Asp Val Cys Val Ser Ala Leu Gly Ala Asp Pro Ser Ser Ala
                 70                  75                  80 acc gcc gac gtc cgc ggg ctc tcg acc atc gcc gtg tcc gcg gcg gcc      348
Thr Ala Asp Val Arg Gly Leu Ser Thr Ile Ala Val Ser Ala Ala Ala
                 85                  90                  95 gcc aac gcc tcg ggc ggc gcc gcc acg gcc gcg gcg ctc gcc aac ggc      396
Ala Asn Ala Ser Gly Gly Ala Ala Thr Ala Ala Ala Leu Ala Asn Gly
            100                 105                 110 acc ggc acc gcg tcg tcg tcc aac gcg cag gcg gcc cct gcc acg gcc      444
Thr Gly Thr Ala Ser Ser Ser Asn Ala Gln Ala Ala Pro Ala Thr Ala
        115                 120                 125 tcc gcc gcc gcg gcg ctg ctc cgc acg tgc gca gcc aag tac ggc cag      492
Ser Ala Ala Ala Ala Leu Leu Arg Thr Cys Ala Ala Lys Tyr Gly Gln
130                 135                 140                 145 gcc cgg gac gcg ctg gcc gcc gcc ggg gac tcc atc gcg cag cag gac      540
Ala Arg Asp Ala Leu Ala Ala Ala Gly Asp Ser Ile Ala Gln Gln Asp
                150                 155                 160 tac gac gtg gcg tcc gtg cac gtg agc gcc gcc gcc gag tac ccg cag      588
Tyr Asp Val Ala Ser Val His Val Ser Ala Ala Ala Glu Tyr Pro Gln
```

```
Tyr Asp Val Ala Ser Val His Val Ser Ala Ala Glu Tyr Pro Gln
            165                 170                 175 gtg tgt agg gtg ctg ttc cgg cgg cag aag ccc ggg cag tac ccc gcg        636
Val Cys Arg Val Leu Phe Arg Arg Gln Lys Pro Gly Gln Tyr Pro Ala
            180                 185                 190 gag ctg gcg gcg agg gag gag acg ctc agg cag ctc tgc tcc gtc gcg        684
Glu Leu Ala Ala Arg Glu Glu Thr Leu Arg Gln Leu Cys Ser Val Ala
        195                 200                 205 ctc gac atc atc ggg ctc gcc tcc acc aac acc aac taa taagctagca         733
Leu Asp Ile Ile Gly Leu Ala Ser Thr Asn Thr Asn *
210                 215                 220 gcagtggcgt ggcggcgaga aagagagga agattaaaaa aaagtagcac cttttctttt        793
ttggtttaat tactgtacgt attatattaa ttagcagggc acatgcacgc agatgcatat        853
ttaaattata aaaggttgg tgtgcctgcc caatcaccgt ttgaagaatt atttgagcag        913
cttaaaaaaa aaaaaaaaaa aaaaaaaaaa aaaaaaaaaa aaaaaaaaaa aaaaaaaaaa        973
aactcgag                                                               981

<210> SEQ ID NO 5
<211> LENGTH: 221
<212> TYPE: PRT
<213> ORGANISM: Zea mays

<400> SEQUENCE: 5

Met Ala Thr Thr Lys Arg Glu Lys Val Ile Leu Val Leu Leu Phe Ser
1                   5                  10                  15

Leu Thr Met Leu Pro Leu Ser Thr Leu Gly Thr Arg Ser Gly Pro Ala
                20                  25                  30

Ala Val Gln His His Gly His Gly Gly Thr Thr Lys His Pro Ser Pro
            35                  40                  45

Pro Ser Pro Ala Thr Ala Ala Leu Val Arg Ser Thr Cys Asn Ser Thr
        50                  55                  60

Ala Tyr Tyr Asp Val Cys Val Ser Ala Leu Gly Ala Asp Pro Ser Ser
65                  70                  75                  80

Ala Thr Ala Asp Val Arg Gly Leu Ser Thr Ile Ala Val Ser Ala Ala
                85                  90                  95

Ala Ala Asn Ala Ser Gly Gly Ala Ala Thr Ala Ala Leu Ala Asn
            100                 105                 110

Gly Thr Gly Thr Ala Ser Ser Ser Asn Ala Gln Ala Ala Pro Ala Thr
        115                 120                 125

Ala Ser Ala Ala Ala Leu Leu Arg Thr Cys Ala Ala Lys Tyr Gly
130                 135                 140

Gln Ala Arg Asp Ala Leu Ala Ala Ala Gly Asp Ser Ile Ala Gln Gln
145                 150                 155                 160

Asp Tyr Asp Val Ala Ser Val His Val Ser Ala Ala Glu Tyr Pro
                165                 170                 175

Gln Val Cys Arg Val Leu Phe Arg Arg Gln Lys Pro Gly Gln Tyr Pro
            180                 185                 190

Ala Glu Leu Ala Ala Arg Glu Glu Thr Leu Arg Gln Leu Cys Ser Val
        195                 200                 205

Ala Leu Asp Ile Ile Gly Leu Ala Ser Thr Asn Thr Asn
    210                 215                 220

<210> SEQ ID NO 6
<211> LENGTH: 666
<212> TYPE: DNA
```

-continued

```
<213> ORGANISM: Zea mays

<400> SEQUENCE: 6
atggcaacca ccaagaggga gaaggtcatc ctcgtcctgc tgttctccct gacgatgctc      60
cctctcagca ccctcggcac ccgctccggc ccggcggccg tgcagcacca cggccacggc     120
ggcaccacca agcacccctc gcctccttca ccagccacgg cggcgctggt acgcagcacg     180
tgtaactcca cggcgtacta cgacgtgtgc gtgtccgcgc tgggcgccga cccgtccagc     240
gccaccgccg acgtccgcgg gctctcgacc atcgccgtgt ccgcggcggc cgccaacgcc     300
tcgggcggcg ccgccacggc cgcggcgctc gccaacggca ccggcaccgc gtcgtcgtcc     360
aacgcgcagg cggcccctgc cacggcctcc gccgccgcgg cgctgctccg cacgtgcgca     420
gccaagtacg gccaggcccg ggacgcgctg gccgccgccg ggactccat cgcgcagcag      480 gactacgacg tggcgtccgt gcacgtgagc ccgccgccg agtaccccgca ggtgtgtagg     540 gtgctgttcc ggcggcagaa gcccgggcag taccccgcg agctggcggc gagggaggag     600
acgctcaggc agctctgctc cgtcgcgctc gacatcatcg ggctcgcctc caccaacacc     660
aactaa                                                                666

<210> SEQ ID NO 7
<211> LENGTH: 779
<212> TYPE: DNA
<213> ORGANISM: Vitis L
<220> FEATURE:
<221> NAME/KEY: CDS
<222> LOCATION: (6)...(644)

<400> SEQUENCE: 7 ctgag atg gaa tct ttc aca tgc cta aag cta tcc tct tcc cgt ggc ctt       50
      Met Glu Ser Phe Thr Cys Leu Lys Leu Ser Ser Ser Arg Gly Leu
      1               5                   10                  15 gca gct att gtt gct ctc ttc ttc ttc tac ctc tca ctc aca aca cca         98
Ala Ala Ile Val Ala Leu Phe Phe Phe Tyr Leu Ser Leu Thr Thr Pro
             20                  25                  30 tgc tcg gcg gcc tca cca gag ccc cat ccc cct acc aat act aca caa        146
Cys Ser Ala Ala Ser Pro Glu Pro His Pro Pro Thr Asn Thr Thr Gln
         35                  40                  45 ttc atc aga acc tca tgc gga gtg act atg tac cct aag cta tgc ttc        194
Phe Ile Arg Thr Ser Cys Gly Val Thr Met Tyr Pro Lys Leu Cys Phe
     50                  55                  60 aaa acc ctc tcg gct tat gcc agc acc atc caa aca agc cat atg gag        242
Lys Thr Leu Ser Ala Tyr Ala Ser Thr Ile Gln Thr Ser His Met Glu
 65                  70                  75 ttg gcc aat gca gcc ctc tgt gtg agc cta aag ggc gct caa tcc tct        290
Leu Ala Asn Ala Ala Leu Cys Val Ser Leu Lys Gly Ala Gln Ser Ser
 80                  85                  90                  95 tca aac aag gta ctg aag tta tca aaa ggg cag ggg cta agc cgt aga        338
Ser Asn Lys Val Leu Lys Leu Ser Lys Gly Gln Gly Leu Ser Arg Arg
            100                 105                 110 gaa gcc gca gcg ata acg gat tgc att gag aac atg cag gac tcg gtg        386
Glu Ala Ala Ala Ile Thr Asp Cys Ile Glu Asn Met Gln Asp Ser Val
        115                 120                 125 gat gag ctc caa caa tct ctg gtg gcg atg aag gac ctt caa ggg cct        434
Asp Glu Leu Gln Gln Ser Leu Val Ala Met Lys Asp Leu Gln Gly Pro
    130                 135                 140 gat ttt caa atg aaa atg agt gat ata gtg aca tgg gtg agt gca gct        482
Asp Phe Gln Met Lys Met Ser Asp Ile Val Thr Trp Val Ser Ala Ala
145                 150                 155
```

```
ctg aca gat gaa gac aca tgc atg gat gga ttc gca gag cat gcc atg    530
Leu Thr Asp Glu Asp Thr Cys Met Asp Gly Phe Ala Glu His Ala Met
160                 165                 170                 175 aaa ggg gac ctt aag agc act att agg agc aat att gtg agt gtt gct    578
Lys Gly Asp Leu Lys Ser Thr Ile Arg Ser Asn Ile Val Ser Val Ala
            180                 185                 190 cag tta acc agc aat gct ttg gcc atc atc aac aag ttt cta tct att    626
Gln Leu Thr Ser Asn Ala Leu Ala Ile Ile Asn Lys Phe Leu Ser Ile
        195                 200                 205 cag ggc aat caa ctc taa gttactgtgt cctatgtgtc tactactagt           674
Gln Gly Asn Gln Leu *
    210 ataattctaa ttaaaagttc ttcagcgtgt ttatgtagta tccatgtgta atgttattgt  734 aaagaaatat ttgctaaaaa aaaaaaaaaa aaaaaaaaaa aaaaa                  779

<210> SEQ ID NO 8
<211> LENGTH: 212
<212> TYPE: PRT
<213> ORGANISM: Vitis L

<400> SEQUENCE: 8

Met Glu Ser Phe Thr Cys Leu Lys Leu Ser Ser Ser Arg Gly Leu Ala
1               5                   10                  15

Ala Ile Val Ala Leu Phe Phe Tyr Leu Ser Leu Thr Thr Pro Cys
            20                  25                  30

Ser Ala Ala Ser Pro Glu Pro His Pro Pro Thr Asn Thr Gln Phe
        35                  40                  45

Ile Arg Thr Ser Cys Gly Val Thr Met Tyr Pro Lys Leu Cys Phe Lys
    50                  55                  60

Thr Leu Ser Ala Tyr Ala Ser Thr Ile Gln Thr Ser His Met Glu Leu
65                  70                  75                  80

Ala Asn Ala Ala Leu Cys Val Ser Leu Lys Gly Ala Gln Ser Ser Ser
                85                  90                  95

Asn Lys Val Leu Lys Leu Ser Lys Gly Gln Gly Leu Ser Arg Arg Glu
            100                 105                 110

Ala Ala Ala Ile Thr Asp Cys Ile Glu Asn Met Gln Asp Ser Val Asp
        115                 120                 125

Glu Leu Gln Gln Ser Leu Val Ala Met Lys Asp Leu Gln Gly Pro Asp
    130                 135                 140

Phe Gln Met Lys Met Ser Asp Ile Val Thr Trp Val Ser Ala Ala Leu
145                 150                 155                 160

Thr Asp Glu Asp Thr Cys Met Asp Gly Phe Ala Glu His Ala Met Lys
                165                 170                 175

Gly Asp Leu Lys Ser Thr Ile Arg Ser Asn Ile Val Ser Val Ala Gln
            180                 185                 190

Leu Thr Ser Asn Ala Leu Ala Ile Ile Asn Lys Phe Leu Ser Ile Gln
        195                 200                 205

Gly Asn Gln Leu
    210

<210> SEQ ID NO 9
<211> LENGTH: 639
<212> TYPE: DNA
<213> ORGANISM: Vitis l

<400> SEQUENCE: 9
atggaatctt tcacatgcct aaagctatcc tcttcccgtg gccttgcagc tattgttgct    60
```

```
ctcttcttct tctacctctc actcacaaca ccatgctcgg cggcctcacc agagccccat    120 cccctacca atactacaca attcatcaga acctcatgcg gagtgactat gtacccaag     180 ctatgcttca aaccctctc ggcttatgcc agcaccatcc aaacaagcca tatggagttg    240
gccaatgcag ccctctgtgt gagcctaaag ggcgctcaat cctcttcaaa caaggtactg    300
aagttatcaa aagggcaggg gctaagccgt agagaagccg cagcgataac ggattgcatt    360
gagaacatgc aggactcggt ggatgagctc aacaatctc tggtggcgat gaaggacctt    420
caagggcctg attttcaaat gaaaatgagt gatatagtga catgggtgag tgcagctctg    480
acagatgaag acacatgcat ggatggattc gcagagcatg ccatgaaagg ggaccttaag    540
agcactatta ggagcaatat tgtgagtgtt gctcagttaa ccagcaatgc tttggccatc    600
atcaacaagt ttctatctat tcagggcaat caactctaa                          639

<210> SEQ ID NO 10
<211> LENGTH: 633
<212> TYPE: DNA
<213> ORGANISM: Vitis L
<220> FEATURE:
<221> NAME/KEY: CDS
<222> LOCATION: (6)...(548)

<400> SEQUENCE: 10 gaaaa atg aag cat tca tta gtc cta atc tat gca tgt att tct ctt ctt     50
      Met Lys His Ser Leu Val Leu Ile Tyr Ala Cys Ile Ser Leu Leu
      1               5                   10                  15 ctc ctc ttc cat tct tcg ctt tcc tgt caa ctc atc cat caa aca tgc       98
Leu Leu Phe His Ser Ser Leu Ser Cys Gln Leu Ile His Gln Thr Cys
            20                  25                  30 aag aga att gca gac aat gat ccc aat gtg agc tac aat tta tgc gtc      146
Lys Arg Ile Ala Asp Asn Asp Pro Asn Val Ser Tyr Asn Leu Cys Val
        35                  40                  45 atg agc ctt gaa tca aat ccc atg agt gca aat gcg agc ctt gaa gaa      194
Met Ser Leu Glu Ser Asn Pro Met Ser Ala Asn Ala Ser Leu Glu Glu
    50                  55                  60 ctt gga gtc atc gca gtc gag cta gcc ttg tct aat gcg aca tac atc      242
Leu Gly Val Ile Ala Val Glu Leu Ala Leu Ser Asn Ala Thr Tyr Ile
65                  70                  75 aat tgg tac att agc aat aag ctt ttg cag gag aaa ggg ttt gat cca      290
Asn Trp Tyr Ile Ser Asn Lys Leu Leu Gln Glu Lys Gly Phe Asp Pro
 80                  85                  90                  95 ttt gcc gag gct tgc cta aaa gat tgt cat gaa ctt tac tcc gac gcc      338
Phe Ala Glu Ala Cys Leu Lys Asp Cys His Glu Leu Tyr Ser Asp Ala
                100                 105                 110 atc cct gag tta aaa gat gtg ctc gat gat ttt aag gac aaa gac tac      386
Ile Pro Glu Leu Lys Asp Val Leu Asp Asp Phe Lys Asp Lys Asp Tyr
            115                 120                 125 tac aag gct aat ata gag ttg agc gca gcc atg gag gcg tcg gct act      434
Tyr Lys Ala Asn Ile Glu Leu Ser Ala Ala Met Glu Ala Ser Ala Thr
        130                 135                 140 tgt gaa gat ggt tac aag gaa agg aaa ggt gaa gtg tct ccc ttg gca      482
Cys Glu Asp Gly Tyr Lys Glu Arg Lys Gly Glu Val Ser Pro Leu Ala
    145                 150                 155 aaa gag gac aac aac ttc ttt caa ttg tgt gca att gct ctt gct ttc      530
Lys Glu Asp Asn Asn Phe Phe Gln Leu Cys Ala Ile Ala Leu Ala Phe
160                 165                 170                 175 act aat atg ttg cat tga tccaatatgt cattgcaaga aatatgaatc             578
Thr Asn Met Leu His *
                180
```

```
tcacaatctt taacctatat atataaggtt tagattaaaa aaaaaaaaaa aaaaa        633
```

<210> SEQ ID NO 11
<211> LENGTH: 180
<212> TYPE: PRT
<213> ORGANISM: Vitis L

<400> SEQUENCE: 11

```
Met Lys His Ser Leu Val Leu Ile Tyr Ala Cys Ile Ser Leu Leu Leu
 1               5                  10                  15

Leu Phe His Ser Ser Leu Ser Cys Gln Leu Ile His Gln Thr Cys Lys
            20                  25                  30

Arg Ile Ala Asp Asn Asp Pro Asn Val Ser Tyr Asn Leu Cys Val Met
        35                  40                  45

Ser Leu Glu Ser Asn Pro Met Ser Ala Asn Ala Ser Leu Glu Glu Leu
    50                  55                  60

Gly Val Ile Ala Val Glu Leu Ala Leu Ser Asn Ala Thr Tyr Ile Asn
65                  70                  75                  80

Trp Tyr Ile Ser Asn Lys Leu Leu Gln Glu Lys Gly Phe Asp Pro Phe
                85                  90                  95

Ala Glu Ala Cys Leu Lys Asp Cys His Glu Leu Tyr Ser Asp Ala Ile
            100                 105                 110

Pro Glu Leu Lys Asp Val Leu Asp Asp Phe Lys Asp Lys Asp Tyr Tyr
        115                 120                 125

Lys Ala Asn Ile Glu Leu Ser Ala Ala Met Glu Ala Ser Ala Thr Cys
    130                 135                 140

Glu Asp Gly Tyr Lys Glu Arg Lys Gly Glu Val Ser Pro Leu Ala Lys
145                 150                 155                 160

Glu Asp Asn Asn Phe Phe Gln Leu Cys Ala Ile Ala Leu Ala Phe Thr
                165                 170                 175

Asn Met Leu His
            180
```

<210> SEQ ID NO 12
<211> LENGTH: 543
<212> TYPE: DNA
<213> ORGANISM: Vitis l

<400> SEQUENCE: 12

```
atgaagcatt cattagtcct aatctatgca tgtatttctc ttcttctcct cttccattct    60
tcgctttcct gtcaactcat ccatcaaaca tgcaagagaa ttgcagacaa tgatcccaat   120
gtgagctaca atttatgcgt catgagcctt gaatcaaatc ccatgagtgc aaatgcgagc   180
cttgaagaac ttggagtcat cgcagtcgag ctagccttgt ctaatgcgac atacatcaat   240
tggtacatta gcaataagct tttgcaggag aaagggtttg atccatttgc cgaggcttgc   300
ctaaaagatt gtcatgaact ttactccgac gccatccctg agttaaaaga tgtgctcgat   360
gattttaagg acaagactac tacaaggct aatatagagt tgagcgcagc catggaggcg   420
tcggctactt gtgaagatgg ttacaaggaa aggaaaggtg aagtgtctcc cttggcaaaa   480
gaggacaaca acttctttca attgtgtgca attgctcttg ctttcactaa tatgttgcat   540
tga                                                                 543
```

<210> SEQ ID NO 13
<211> LENGTH: 844
<212> TYPE: DNA

<213> ORGANISM: Vitis L
<220> FEATURE:
<221> NAME/KEY: CDS
<222> LOCATION: (99)...(647)

<400> SEQUENCE: 13

```
ctctagactc cccccccgtc cttagcctct ctgcatgtct tgaaacaaag ctgatttta    60 tccccctgtct gttcaaaaac ttgggcacaa tacctctc atg ggt ttt gct ggt ttg  116
                                           Met Gly Phe Ala Gly Leu
                                            1               5 ttg ttc ctc ttt ctt ctc atg tcg ctc ctt cag tta ttt cat ccc cag     164
Leu Phe Leu Phe Leu Leu Met Ser Leu Leu Gln Leu Phe His Pro Gln
         10                  15                  20 ctt gtt ctt gtg agc ggt gac tat gat ttg atc cag aaa act tgt aga     212
Leu Val Leu Val Ser Gly Asp Tyr Asp Leu Ile Gln Lys Thr Cys Arg
     25                  30                  35 agc acc aaa tac tac gac ctt tgc atc tca tcc ctc aaa tct gat ccc     260
Ser Thr Lys Tyr Tyr Asp Leu Cys Ile Ser Ser Leu Lys Ser Asp Pro
 40                  45                  50 aac agc ccc aat gcc gac acc aag gga ttg gcg atg att atg gtt gga    308
Asn Ser Pro Asn Ala Asp Thr Lys Gly Leu Ala Met Ile Met Val Gly
 55                  60                  65                  70 att gga gag gct aat gcc act gcc att tcc tct tac ttg tcc tcc caa    356
Ile Gly Glu Ala Asn Ala Thr Ala Ile Ser Ser Tyr Leu Ser Ser Gln
             75                  80                  85 ttg gtc ggc tct gct aat gat tca tca atg aag aag atc ctt aag gaa    404
Leu Val Gly Ser Ala Asn Asp Ser Ser Met Lys Lys Ile Leu Lys Glu
         90                  95                 100 tgc gtc aac agg tac aac tat tct agc gat gcg ctc caa gct tcg ctc    452
Cys Val Asn Arg Tyr Asn Tyr Ser Ser Asp Ala Leu Gln Ala Ser Leu
     105                 110                 115 caa gct ttg acc atg gag gct tat gac tat gct tac gtg cat gtt ata    500
Gln Ala Leu Thr Met Glu Ala Tyr Asp Tyr Ala Tyr Val His Val Ile
 120                 125                 130 gca gcc gca gat tat ccc aat gcc tgc cgc aat tct ttt aaa agg tgc    548
Ala Ala Ala Asp Tyr Pro Asn Ala Cys Arg Asn Ser Phe Lys Arg Cys
135                 140                 145                 150 cca aga ttg cct tat cca ccg gaa ctc ggg cta aga gaa gat gtt ttg    596
Pro Arg Leu Pro Tyr Pro Pro Glu Leu Gly Leu Arg Glu Asp Val Leu
                 155                 160                 165 aag cat ctg tgt gat gtg gtc ttg gga att att gat ctt ctt gat tgg    644
Lys His Leu Cys Asp Val Val Leu Gly Ile Ile Asp Leu Leu Asp Trp
             170                 175                 180 taa tggtctcccc tttgcttcat tcttggtgtt taatcaacat attgcagact         697
* tccaaaaata ttcgttgtgt ttctttgatc tttgtacaat gacttccacc ttgtctttga  757
agccaaaccg tgctttgtaa ctgtagcgtt tgataagctt aaagcttata taactttatt  817
tgtctgcaaa aaaaaaaaa aaaaaa                                        844
```

<210> SEQ ID NO 14
<211> LENGTH: 182
<212> TYPE: PRT
<213> ORGANISM: Vitis L

<400> SEQUENCE: 14

```
Met Gly Phe Ala Gly Leu Leu Phe Leu Phe Leu Leu Met Ser Leu Leu
 1               5                  10                  15

Gln Leu Phe His Pro Gln Leu Val Leu Val Ser Gly Asp Tyr Asp Leu
             20                  25                  30
```

```
Ile Gln Lys Thr Cys Arg Ser Thr Lys Tyr Tyr Asp Leu Cys Ile Ser
            35                  40                  45

Ser Leu Lys Ser Asp Pro Asn Ser Pro Asn Ala Asp Thr Lys Gly Leu
 50                  55                  60

Ala Met Ile Met Val Gly Ile Gly Glu Ala Asn Ala Thr Ala Ile Ser
 65                  70                  75                  80

Ser Tyr Leu Ser Ser Gln Leu Val Gly Ser Ala Asn Asp Ser Ser Met
                 85                  90                  95

Lys Lys Ile Leu Lys Glu Cys Val Asn Arg Tyr Asn Tyr Ser Ser Asp
            100                 105                 110

Ala Leu Gln Ala Ser Leu Gln Ala Leu Thr Met Glu Ala Tyr Asp Tyr
            115                 120                 125

Ala Tyr Val His Val Ile Ala Ala Ala Asp Tyr Pro Asn Ala Cys Arg
130                 135                 140

Asn Ser Phe Lys Arg Cys Pro Arg Leu Pro Tyr Pro Pro Glu Leu Gly
145                 150                 155                 160

Leu Arg Glu Asp Val Leu Lys His Leu Cys Asp Val Val Leu Gly Ile
                165                 170                 175

Ile Asp Leu Leu Asp Trp
            180
```

<210> SEQ ID NO 15
<211> LENGTH: 549
<212> TYPE: DNA
<213> ORGANISM: Vitis 1

<400> SEQUENCE: 15

```
atgggttttg ctggtttgtt gttcctcttt cttctcatgt cgctccttca gttatttcat    60
ccccagcttg ttcttgtgag cggtgactat gatttgatcc agaaaacttg tagaagcacc   120
aaatactacg acctttgcat ctcatccctc aaatctgatc ccaacagccc caatgccgac   180
accaagggat tggcgatgat tatggttgga attggagagg ctaatgccac tgccatttcc   240
tcttacttgt cctcccaatt ggtcggctct gctaatgatt catcaatgaa gaagatcctt   300
aaggaatgcg tcaacaggta caactattct agcgatgcgc tccaagcttc gctccaagct   360
ttgaccatgg aggcttatga ctatgcttac gtgcatgtta tagcagccgc agattatccc   420
aatgcctgcc gcaattcttt taaaaggtgc ccaagattgc cttatccacc ggaactcggg   480
ctaagagaag atgttttgaa gcatctgtgt gatgtggtct tgggaattat tgatcttctt   540
gattggtaa                                                            549
```

<210> SEQ ID NO 16
<211> LENGTH: 775
<212> TYPE: DNA
<213> ORGANISM: Vitis 1
<220> FEATURE:
<221> NAME/KEY: CDS
<222> LOCATION: (121)...(669)

<400> SEQUENCE: 16

```
ctcatactta tagtcttaca caacatctat ctatataaag tatgtccctc tcttgatcag    60
aaaaccaaag aagacaaaaa ggaaacagaa aaatttaagc cttgaaagtt ggaaagagcg   120 atg agg ctt tcc tcc agt ttc ttt ctc ctc acc ctc gta ttc tta ttc   168
Met Arg Leu Ser Ser Ser Phe Phe Leu Leu Thr Leu Val Phe Leu Phe
  1               5                  10                  15 ttc atc ttt ccc gca gca acc agt tgt tgc acc aag ctc ata gat gag   216
```

```
Phe Ile Phe Pro Ala Ala Thr Ser Cys Cys Thr Lys Leu Ile Asp Glu
             20                  25                  30 acc tgc aag aac tct tca cac aat gac agt aac ttc agt tac agg ttc       264
Thr Cys Lys Asn Ser Ser His Asn Asp Ser Asn Phe Ser Tyr Arg Phe
         35                  40                  45 tgc aag act tcc ctc cag gca gct ccg gcc agc cgc tgc gcc agt ctc       312
Cys Lys Thr Ser Leu Gln Ala Ala Pro Ala Ser Arg Cys Ala Ser Leu
 50                  55                  60 cgg gga ctg ggg ttg atc gcc atc aga tta ttc cgg gat aac gcc acc       360
Arg Gly Leu Gly Leu Ile Ala Ile Arg Leu Phe Arg Asp Asn Ala Thr
 65                  70                  75                  80 gac acc aga tgt ttc atc aga gaa ctg ctc gga aag aag ggg ttg gac       408
Asp Thr Arg Cys Phe Ile Arg Glu Leu Leu Gly Lys Lys Gly Leu Asp
                 85                  90                  95 aca tct gtg aag atg cgt ttg gaa gat tgt ttg gac atg tat tcg gat       456
Thr Ser Val Lys Met Arg Leu Glu Asp Cys Leu Asp Met Tyr Ser Asp
            100                 105                 110 gga gtc gaa tcc cta aca cag gcc att aaa ggg tac agg gct ggg gag       504
Gly Val Glu Ser Leu Thr Gln Ala Ile Lys Gly Tyr Arg Ala Gly Glu
        115                 120                 125 tat ttc gat gct aat gtc caa gtt tcg ggt gct atg act tat gct agt       552
Tyr Phe Asp Ala Asn Val Gln Val Ser Gly Ala Met Thr Tyr Ala Ser
130                 135                 140 act tgt gaa gat ggt ttc cag gag aag gaa ggt ttg gtt tcg ccg ttg       600
Thr Cys Glu Asp Gly Phe Gln Glu Lys Glu Gly Leu Val Ser Pro Leu
145                 150                 155                 160 acg aag caa aac gac gat gct ttt cag ttg ggt gcg ctc tct ctt tcg       648
Thr Lys Gln Asn Asp Asp Ala Phe Gln Leu Gly Ala Leu Ser Leu Ser
                165                 170                 175 att atg aat aag cag aag tga ttcatggctg gctgattggc tggctttgtt         699
Ile Met Asn Lys Gln Lys  *
                180 ttttttttaat tctgaggcaa tgcttctctt tttctaaata attaatattt actttcacaa   759
aaaaaaaaaa aaaaaa                                                    775

<210> SEQ ID NO 17
<211> LENGTH: 182
<212> TYPE: PRT
<213> ORGANISM: Vitis 1

<400> SEQUENCE: 17

Met Arg Leu Ser Ser Ser Phe Phe Leu Leu Thr Leu Val Phe Leu Phe
  1               5                  10                  15

Phe Ile Phe Pro Ala Ala Thr Ser Cys Cys Thr Lys Leu Ile Asp Glu
             20                  25                  30

Thr Cys Lys Asn Ser Ser His Asn Asp Ser Asn Phe Ser Tyr Arg Phe
         35                  40                  45

Cys Lys Thr Ser Leu Gln Ala Ala Pro Ala Ser Arg Cys Ala Ser Leu
 50                  55                  60

Arg Gly Leu Gly Leu Ile Ala Ile Arg Leu Phe Arg Asp Asn Ala Thr
 65                  70                  75                  80

Asp Thr Arg Cys Phe Ile Arg Glu Leu Leu Gly Lys Lys Gly Leu Asp
                 85                  90                  95

Thr Ser Val Lys Met Arg Leu Glu Asp Cys Leu Asp Met Tyr Ser Asp
            100                 105                 110

Gly Val Glu Ser Leu Thr Gln Ala Ile Lys Gly Tyr Arg Ala Gly Glu
        115                 120                 125
```

```
Tyr Phe Asp Ala Asn Val Gln Val Ser Gly Ala Met Thr Tyr Ala Ser
    130                 135                 140

Thr Cys Glu Asp Gly Phe Gln Glu Lys Glu Gly Leu Val Ser Pro Leu
145                 150                 155                 160

Thr Lys Gln Asn Asp Asp Ala Phe Gln Leu Gly Ala Leu Ser Leu Ser
                165                 170                 175

Ile Met Asn Lys Gln Lys
            180

<210> SEQ ID NO 18
<211> LENGTH: 549
<212> TYPE: DNA
<213> ORGANISM: Vitis l

<400> SEQUENCE: 18
atgaggcttt cctccagttt ctttctcctc accctcgtat tcttattctt catctttccc      60
gcagcaacca gttgttgcac caagctcata gatgagacct gcaagaactc ttcacacaat     120
gacagtaact tcagttacag gttctgcaag acttccctcc aggcagctcc ggccagccgc     180
tgcgccagtc tccggggact ggggttgatc gccatcagat tattccggga taacgccacc     240
gacaccagat gtttcatcag agaactgctc ggaaagaagg ggttggacac atctgtgaag     300
atgcgtttgg aagattgttt ggacatgtat tcggatggag tcgaatccct aacacaggcc     360
attaaagggt acagggctgg ggagtatttc gatgctaatg tccaagtttc gggtgctatg     420
acttatgcta gtacttgtga agatggtttc caggagaagg aaggtttggt ttcgccgttg     480
acgaagcaaa acgacgatgc ttttcagttg ggtgcgctct ctctttcgat tatgaataag     540
cagaagtga                                                             549

<210> SEQ ID NO 19
<211> LENGTH: 686
<212> TYPE: DNA
<213> ORGANISM: Vitis L
<220> FEATURE:
<221> NAME/KEY: CDS
<222> LOCATION: (11)...(547)

<400> SEQUENCE: 19
gctatcatcc atg gct tct gta att ctt ctt ttt ctt ctc act ctt tca         49
            Met Ala Ser Val Ile Leu Leu Phe Leu Leu Thr Leu Ser
            1               5                   10 tcc cct ctc ttc ttt ggc caa aca ctc aac ccc gta gag gca gga gac         97
Ser Pro Leu Phe Phe Gly Gln Thr Leu Asn Pro Val Glu Ala Gly Asp
 15                  20                  25 aaa cta att gaa agt gca tgc cac act gct gag gta cca gta gta tgc        145
Lys Leu Ile Glu Ser Ala Cys His Thr Ala Glu Val Pro Val Val Cys
 30                  35                  40                  45 atg cag tgt gta aaa tct gac gag cgt tcg ggg aaa gcc gat gcg gta        193
Met Gln Cys Val Lys Ser Asp Glu Arg Ser Gly Lys Ala Asp Ala Val
             50                  55                  60 ggg att gcc aac atc atc gtc gac tgt ttg atg agc cac tct agc tac        241
Gly Ile Ala Asn Ile Ile Val Asp Cys Leu Met Ser His Ser Ser Tyr
         65                  70                  75 ttg gca agc aac atg tcg aat tta ggt tct aat cct gaa cac aat gcc        289
Leu Ala Ser Asn Met Ser Asn Leu Gly Ser Asn Pro Glu His Asn Ala
     80                  85                  90 aca aaa tca gcc tat gaa cat tgc ttc ctg cac tgt tct gat gca aag        337
Thr Lys Ser Ala Tyr Glu His Cys Phe Leu His Cys Ser Asp Ala Lys
 95                  100                 105
```

```
aag gcg cta aat tca gca gct ttg gag cta aag aat ggc agc tat gat       385
Lys Ala Leu Asn Ser Ala Ala Leu Glu Leu Lys Asn Gly Ser Tyr Asp
110             115                 120                 125 agc gct gaa ctg tcc ttg cgc gaa gca gcg cta tat caa ggc aca tgc       433
Ser Ala Glu Leu Ser Leu Arg Glu Ala Ala Leu Tyr Gln Gly Thr Cys
            130                 135                 140 cga tac gag ttt gtg agt tca aat gag act tat gtg cca cct aat gtt       481
Arg Tyr Glu Phe Val Ser Ser Asn Glu Thr Tyr Val Pro Pro Asn Val
        145                 150                 155 tac tat gat ctg aag gtc ttt gat ata ctt act gtg gct gcc ttt aga       529
Tyr Tyr Asp Leu Lys Val Phe Asp Ile Leu Thr Val Ala Ala Phe Arg
160                 165                 170 att ata gag aag ctt tga ttaagagttt tggagggttt tcacctaatt              577
Ile Ile Glu Lys Leu *
    175 gctcatcatc catgaaaaat aaagtttcat gttgactagt agacatgtaa catgaaatat     637 tgagacataa catacacctc cttatcatct aaaaaaaaaa aaaaaaaa                  686

<210> SEQ ID NO 20
<211> LENGTH: 178
<212> TYPE: PRT
<213> ORGANISM: Vitis L

<400> SEQUENCE: 20

Met Ala Ser Val Ile Leu Leu Phe Leu Leu Thr Leu Ser Ser Pro Leu
1               5                   10                  15

Phe Phe Gly Gln Thr Leu Asn Pro Val Glu Ala Gly Asp Lys Leu Ile
            20                  25                  30

Glu Ser Ala Cys His Thr Ala Glu Val Pro Val Cys Met Gln Cys
        35                  40                  45

Val Lys Ser Asp Glu Arg Ser Gly Lys Ala Asp Ala Val Gly Ile Ala
    50                  55                  60

Asn Ile Ile Val Asp Cys Leu Met Ser His Ser Ser Tyr Leu Ala Ser
65                  70                  75                  80

Asn Met Ser Asn Leu Gly Ser Asn Pro Glu His Asn Ala Thr Lys Ser
                85                  90                  95

Ala Tyr Glu His Cys Phe Leu His Cys Ser Asp Ala Lys Lys Ala Leu
            100                 105                 110

Asn Ser Ala Ala Leu Glu Leu Lys Asn Gly Ser Tyr Asp Ser Ala Glu
        115                 120                 125

Leu Ser Leu Arg Glu Ala Ala Leu Tyr Gln Gly Thr Cys Arg Tyr Glu
    130                 135                 140

Phe Val Ser Ser Asn Glu Thr Tyr Val Pro Pro Asn Val Tyr Tyr Asp
145                 150                 155                 160

Leu Lys Val Phe Asp Ile Leu Thr Val Ala Ala Phe Arg Ile Ile Glu
                165                 170                 175

Lys Leu

<210> SEQ ID NO 21
<211> LENGTH: 537
<212> TYPE: DNA
<213> ORGANISM: Vitis l

<400> SEQUENCE: 21
atggcttctg taattcttct ttttcttctc actctttcat cccctctctt ctttggccaa     60
acactcaacc ccgtagaggc aggagacaaa ctaattgaaa gtgcatgcca cactgctgag    120
```

```
gtaccagtag tatgcatgca gtgtgtaaaa tctgacgagc gttcgggaa agccgatgcg      180 gtagggattg ccaacatcat cgtcgactgt ttgatgagcc actctagcta cttggcaagc      240
aacatgtcga atttaggttc taatcctgaa cacaatgcca caaaatcagc ctatgaacat      300
tgcttcctgc actgttctga tgcaaagaag gcgctaaatt cagcagcttt ggagctaaag      360
aatggcagct atgatagcgc tgaactgtcc ttgcgcgaag cagcgctata tcaaggcaca      420
tgccgatacg agtttgtgag ttcaaatgag acttatgtgc cacctaatgt ttactatgat      480
ctgaaggtct tgatatact tactgtggct gcctttagaa ttatagagaa gctttga         537
```

```
<210> SEQ ID NO 22
<211> LENGTH: 709
<212> TYPE: DNA
<213> ORGANISM: Vitis 1
<220> FEATURE:
<221> NAME/KEY: CDS
<222> LOCATION: (13)...(558)

<400> SEQUENCE: 22
```

```
gaaattaagg aa atg gct tcc ttg agt ggg gta ctg tta ctt gtt cat atc      51
              Met Ala Ser Leu Ser Gly Val Leu Leu Leu Val His Ile
                1               5                  10 tcc ctc atg gcc acc act ctc ttc tac tat cct tca cat gcg atc gga        99
Ser Leu Met Ala Thr Thr Leu Phe Tyr Tyr Pro Ser His Ala Ile Gly
 15                  20                  25 caa gac gtc gtc gag cag gta tgc cag caa acg gag gac tat caa ttc        147
Gln Asp Val Val Glu Gln Val Cys Gln Gln Thr Glu Asp Tyr Gln Phe
 30                  35                  40                  45 tgt ttc aat acc atc ctc aga gat cct cgg act ccg gca gtt aac atg        195
Cys Phe Asn Thr Ile Leu Arg Asp Pro Arg Thr Pro Ala Val Asn Met
                 50                  55                  60 gag ggg ctg tgc ctc ctc agt gtg gca ata acc ata gac cac gtt agg        243
Glu Gly Leu Cys Leu Leu Ser Val Ala Ile Thr Ile Asp His Val Arg
 65                  70                  75 gaa gcg gtg gat aaa ata ccg ggg ctg ctg gag aaa gct act gat cca        291
Glu Ala Val Asp Lys Ile Pro Gly Leu Leu Glu Lys Ala Thr Asp Pro
 80                  85                  90 gtg gac aag caa aga atg acg act tgc caa tcc aac tat gga gca gcg        339
Val Asp Lys Gln Arg Met Thr Thr Cys Gln Ser Asn Tyr Gly Ala Ala
 95                 100                 105 gcg ggg gac ttc cag agg gcg tgg ggc tcg gct tct tca aag gct ttc        387
Ala Gly Asp Phe Gln Arg Ala Trp Gly Ser Ala Ser Ser Lys Ala Phe
110                 115                 120                 125 cat gat gtg ctg ggc tgg gtt cag aag gga agt ggt cag gtt ata aac        435
His Asp Val Leu Gly Trp Val Gln Lys Gly Ser Gly Gln Val Ile Asn
                130                 135                 140 tgt gaa aat ata tac cgg caa agt ccg ccg atc cgt gaa tct ccc ctc        483
Cys Glu Asn Ile Tyr Arg Gln Ser Pro Pro Ile Arg Glu Ser Pro Leu
145                 150                 155 aca gtt gac aac cac aac gtg att aaa tta gca gga att act ttg gtt        531
Thr Val Asp Asn His Asn Val Ile Lys Leu Ala Gly Ile Thr Leu Val
                160                 165                 170 gtt ctt ggt atg ctt ggt gtt cgt tga agatggtgtg tcttccttga              578
Val Leu Gly Met Leu Gly Val Arg  *
175                 180 ggtaaagctc acgttcttgg aattaacgta caataaatgt ggaatgcaat actgttggtt     638
ggtcaataaa aactgatgtg aatttactac tcaaaaaaaa aaaaaaaaaa aaaaaaaaaa     698 aaaaaaaaa a                                                            709
```

<210> SEQ ID NO 23
<211> LENGTH: 181
<212> TYPE: PRT
<213> ORGANISM: Vitis 1

<400> SEQUENCE: 23

Met Ala Ser Leu Ser Gly Val Leu Leu Val His Ile Ser Leu Met
1               5                   10                  15

Ala Thr Thr Leu Phe Tyr Tyr Pro Ser His Ala Ile Gly Gln Asp Val
            20                  25                  30

Val Glu Gln Val Cys Gln Gln Thr Glu Asp Tyr Gln Phe Cys Phe Asn
        35                  40                  45

Thr Ile Leu Arg Asp Pro Arg Thr Pro Ala Val Asn Met Glu Gly Leu
    50                  55                  60

Cys Leu Leu Ser Val Ala Ile Thr Ile Asp His Val Arg Glu Ala Val
65                  70                  75                  80

Asp Lys Ile Pro Gly Leu Leu Glu Lys Ala Thr Asp Pro Val Asp Lys
                85                  90                  95

Gln Arg Met Thr Thr Cys Gln Ser Asn Tyr Gly Ala Ala Ala Gly Asp
            100                 105                 110

Phe Gln Arg Ala Trp Gly Ser Ala Ser Ser Lys Ala Phe His Asp Val
        115                 120                 125

Leu Gly Trp Val Gln Lys Gly Ser Gly Gln Val Ile Asn Cys Glu Asn
    130                 135                 140

Ile Tyr Arg Gln Ser Pro Pro Ile Arg Glu Ser Pro Leu Thr Val Asp
145                 150                 155                 160

Asn His Asn Val Ile Lys Leu Ala Gly Ile Thr Leu Val Val Leu Gly
                165                 170                 175

Met Leu Gly Val Arg
            180

<210> SEQ ID NO 24
<211> LENGTH: 546
<212> TYPE: DNA
<213> ORGANISM: Vitis 1

<400> SEQUENCE: 24
atggcttcct tgagtggggt actgttactt gttcatatct ccctcatggc caccactctc    60
ttctactatc cttcacatgc gatcggacaa gacgtcgtcg agcaggtatg ccagcaaacg   120
gaggactatc aattctgttt caataccatc ctcagagatc ctcggactcc ggcagttaac   180
atggagggc tgtgcctcct cagtgtggca ataaccatag accacgttag ggaagcggtg    240
gataaaatac cggggctgct ggagaaagct actgatccag tggacaagca agaatgacg    300
acttgccaat ccaactatgg agcagcggcg ggggacttcc agagggcgtg gggctcggct   360
tcttcaaagg ctttccatga tgtgctgggc tgggttcaga agggaagtgg tcaggttata   420
aactgtgaaa atatataccg gcaaagtccg ccgatccgtg aatctcccct cacagttgac   480
aaccacaacg tgattaaatt agcaggaatt actttggttg ttcttggtat gcttggtgtt   540
cgttga                                                              546

<210> SEQ ID NO 25
<211> LENGTH: 1067
<212> TYPE: DNA
<213> ORGANISM: Zea mays
<220> FEATURE:
<221> NAME/KEY: CDS -continued

<222> LOCATION: (68)...(691)

<400> SEQUENCE: 25

```
tagacatata ccaacggtaa cgtgttgcat cccattgtaa aagccggcta tcactttcag        60 ggacaaa atg ccc aca tta att att ata aaa ggc cgg cca aat atg gct        109
        Met Pro Thr Leu Ile Ile Ile Lys Gly Arg Pro Asn Met Ala
        1               5                   10 tcc gga acg ccc tac act gcc gtc ggc gtc atc ttc ctc tcc gtc ttc        157
Ser Gly Thr Pro Tyr Thr Ala Val Gly Val Ile Phe Leu Ser Val Phe
15                  20                  25                  30 ctc gtc gcc gcg gca tcc gca ggc cgc acc gcg gca cct gcg gcc gcg        205
Leu Val Ala Ala Ala Ser Ala Gly Arg Thr Ala Ala Pro Ala Ala Ala
                35                  40                  45 ccg tcg agc aag tac tcg ctc gag gaa gcg tgc gag cag acc gcg ggg        253
Pro Ser Ser Lys Tyr Ser Leu Glu Glu Ala Cys Glu Gln Thr Ala Gly
    50                  55                  60 cac gag gac ctg tgc gtg gag acg ctg tcc gcg gac ccg tcg tcc aag        301
His Glu Asp Leu Cys Val Glu Thr Leu Ser Ala Asp Pro Ser Ser Lys
65                  70                  75 act gcc gac act acg ggg ctc gca cgg ttg gcc atc cag gcg gca cag        349
Thr Ala Asp Thr Thr Gly Leu Ala Arg Leu Ala Ile Gln Ala Ala Gln
        80                  85                  90 cgg aac gcg tcg gag acg gcg acc tac ctc tcc agc atc tac gac gac        397
Arg Asn Ala Ser Glu Thr Ala Thr Tyr Leu Ser Ser Ile Tyr Asp Asp
95                  100                 105                 110 gac agc ctt gag aac aag acg gcg cag ctg cag cag tgc ctt gaa aac        445
Asp Ser Leu Glu Asn Lys Thr Ala Gln Leu Gln Gln Cys Leu Glu Asn
                115                 120                 125 tgc ggc gag agg tac gag tcg gcg gtg gag cag ctg tcg gac gcg acg        493
Cys Gly Glu Arg Tyr Glu Ser Ala Val Glu Gln Leu Ser Asp Ala Thr
            130                 135                 140 tcg gcg ctg gac acg ggc gcg tac agc gag tcg gag gag ctg gtg gtg        541
Ser Ala Leu Asp Thr Gly Ala Tyr Ser Glu Ser Glu Glu Leu Val Val
        145                 150                 155 gcg agc cag gct gag gtg agg ctg tgt cag cgt ggc tgc caa gcc gtg        589
Ala Ser Gln Ala Glu Val Arg Leu Cys Gln Arg Gly Cys Gln Ala Val
160                 165                 170 ccg aac cac cgc aac atc ctc tcg gcg cgc aac cgc aac gtc gac cag        637
Pro Asn His Arg Asn Ile Leu Ser Ala Arg Asn Arg Asn Val Asp Gln
175                 180                 185                 190 ctc tgc agc atc gcg ctc gcc atc acc aag ctc atc cac gga ccg cca        685
Leu Cys Ser Ile Ala Leu Ala Ile Thr Lys Leu Ile His Gly Pro Pro
                195                 200                 205 tct tga tacacaggac gtagtaaaca tttagggctt gttcatttcg ccgttaatcc        741
Ser * atgtggattg ggtggtattg agtcggttta attccatagc aagtcaaaat acatcccaat        801
ccatcccaat acacaccaat acacatgaa ttgaaggtgg ttccatactt gtaacgtaat         861
tggtaactaa tgatgacgtt aaatcatatt tgtttaagtt taattataat cagataccac        921
ataaaaaatt aatatcagac tatttaaatt tattaccgct ggtattcaag tgtgaatcat        981
gtggctatat caacttctat tgtaagcaga ttgagagtag tcggtggtta accatattaa       1041
attaaaaaaa aaaaaaaaaa aaaaaa                                            1067
```

<210> SEQ ID NO 26
<211> LENGTH: 207
<212> TYPE: PRT
<213> ORGANISM: Zea mays

<400> SEQUENCE: 26

```
Met Pro Thr Leu Ile Ile Lys Gly Arg Pro Asn Met Ala Ser Gly
 1               5                  10                  15
Thr Pro Tyr Thr Ala Val Gly Val Ile Phe Leu Ser Val Phe Leu Val
             20                  25                  30
Ala Ala Ala Ser Ala Gly Arg Thr Ala Pro Ala Ala Ala Pro Ser
             35                  40                  45
Ser Lys Tyr Ser Leu Glu Glu Ala Cys Glu Gln Thr Ala Gly His Glu
 50                  55                  60
Asp Leu Cys Val Glu Thr Leu Ser Ala Asp Pro Ser Ser Lys Thr Ala
 65                  70                  75                  80
Asp Thr Thr Gly Leu Ala Arg Leu Ala Ile Gln Ala Ala Gln Arg Asn
                 85                  90                  95
Ala Ser Glu Thr Ala Thr Tyr Leu Ser Ser Ile Tyr Asp Asp Asp Ser
                100                 105                 110
Leu Glu Asn Lys Thr Ala Gln Leu Gln Gln Cys Leu Glu Asn Cys Gly
                115                 120                 125
Glu Arg Tyr Glu Ser Ala Val Glu Gln Leu Ser Asp Ala Thr Ser Ala
                130                 135                 140
Leu Asp Thr Gly Ala Tyr Ser Glu Ser Glu Glu Leu Val Val Ala Ser
145                 150                 155                 160
Gln Ala Glu Val Arg Leu Cys Gln Arg Gly Cys Gln Ala Val Pro Asn
                165                 170                 175
His Arg Asn Ile Leu Ser Ala Arg Asn Arg Asn Val Asp Gln Leu Cys
                180                 185                 190
Ser Ile Ala Leu Ala Ile Thr Lys Leu Ile His Gly Pro Pro Ser
                195                 200                 205
```

<210> SEQ ID NO 27
<211> LENGTH: 624
<212> TYPE: DNA
<213> ORGANISM: Zea mays

<400> SEQUENCE: 27

```
atgcccacat taattattat aaaaggccgg ccaaatatgg cttccggaac gccctacact    60
gccgtcggcg tcatcttcct ctccgtcttc ctcgtcgccg cggcatccgc aggccgcacc   120
gcggcacctg cggccgcgcc gtcgagcaag tactcgctcg aggaagcgtg cgagcagacc   180
gcggggcacg aggacctgtg cgtggagacg ctgtccgcgg acccgtcgtc caagactgcc   240
gacactacgg ggctcgcacg gttggccatc caggcggcac agcggaacgc gtcggagacg   300
gcgacctacc tctccagcat ctacgacgac gacagccttg agaacaagac ggcgcagctg   360
cagcagtgcc ttgaaaactg cggcgagagg tacgagtcgg cggtggagca gctgtcggac   420
gcgacgtcgg cgctggacac gggcgcgtac agcgagtcgg aggagctggt ggtggcgagc   480
caggctgagg tgaggctgtg tcagcgtggc tgccaagccg tgccgaacca ccgcaacatc   540
ctctcggcgc gcaaccgcaa cgtcgaccag ctctgcagca tcgcgctcgc catcaccaag   600
ctcatccacg gaccgccatc ttga                                          624
```

<210> SEQ ID NO 28
<211> LENGTH: 1214
<212> TYPE: DNA
<213> ORGANISM: Oryza sativa
<220> FEATURE:
<221> NAME/KEY: CDS
<222> LOCATION: (124)...(810)

<400> SEQUENCE: 28

```
aactagctat ctagcttagc ctcgctaaac caacaccatc gtaaaaatct ctttgatagt      60
tgacatcgag gcagtgatta attaagtagc tagctagtta caggcacaag gagagaaaca     120
```

| | | | | | | | | | | | | | | | | |
|---|---|---|---|---|---|---|---|---|---|---|---|---|---|---|---|---|
| cca | atg | gca | tca | atg | gcg | cca | tcg | gca | atg | gtg | ctc | atc | gtc | ctc | ctc | 168 |
| | Met | Ala | Ser | Met | Ala | Pro | Ser | Ala | Met | Val | Leu | Ile | Val | Leu | Leu | |
| | 1 | | | 5 | | | | | 10 | | | | | 15 | | |
| gtc | ctg | gtg | gtt | ctc | ccg | tcg | agc | act | ctg | tgc | tca | cgg | gcg | ggg | cct | 216 |
| Val | Leu | Val | Val | Leu | Pro | Ser | Ser | Thr | Leu | Cys | Ser | Arg | Ala | Gly | Pro | |
| | | | 20 | | | | | 25 | | | | | 30 | | | |
| tct | tcc | aag | cac | ggc | cat | ggc | ggt | ggc | cac | gcc | aag | cgc | gtg | ccg | cca | 264 |
| Ser | Ser | Lys | His | Gly | His | Gly | Gly | Gly | His | Ala | Lys | Arg | Val | Pro | Pro | |
| | | | 35 | | | | | 40 | | | | | 45 | | | |
| ccg | gcg | tcg | gta | ccg | ccg | ccg | ccg | cca | cca | gcg | ccg | gcg | gcg | | | 312 |
| Pro | Ala | Ser | Val | Pro | Pro | Pro | Pro | Pro | Pro | Ala | Pro | Ala | Ala | | | |
| | | 50 | | | | | 55 | | | | | 60 | | | | |
| ctg | gtg | cgt | gcc | acc | tgc | aac | tcc | acc | tcc | tac | tac | gac | ctc | tgc | gtc | 360 |
| Leu | Val | Arg | Ala | Thr | Cys | Asn | Ser | Thr | Ser | Tyr | Tyr | Asp | Leu | Cys | Val | |
| | 65 | | | | | 70 | | | | | 75 | | | | | |
| gcc | gag | ctg | tcc | gcc | gac | ccg | tcg | agc | gcc | acg | gcc | gac | gtg | cgc | gga | 408 |
| Ala | Glu | Leu | Ser | Ala | Asp | Pro | Ser | Ser | Ala | Thr | Ala | Asp | Val | Arg | Gly | |
| 80 | | | | | 85 | | | | | 90 | | | | | 95 | |
| ctg | tcg | tcc | atc | gcc | gtc | tcc | gcc | gcc | gcc | gcc | aac | gca | tcc | ggg | gcg | 456 |
| Leu | Ser | Ser | Ile | Ala | Val | Ser | Ala | Ala | Ala | Ala | Asn | Ala | Ser | Gly | Ala | |
| | | | 100 | | | | | 105 | | | | | 110 | | | |
| gcg | cag | gcg | gcc | tcg | gcg | ctg | gcg | aac | gcg | acc | gac | gcg | ggg | acg | acg | 504 |
| Ala | Gln | Ala | Ala | Ser | Ala | Leu | Ala | Asn | Ala | Thr | Asp | Ala | Gly | Thr | Thr | |
| | | 115 | | | | | 120 | | | | | 125 | | | | |
| gcg | ggc | gtc | gcc | ggc | gac | ggc | ggc | ggc | gca | gtc | gta | cag | agg | ctg | ctc | 552 |
| Ala | Gly | Val | Ala | Gly | Asp | Gly | Gly | Gly | Ala | Val | Val | Gln | Arg | Leu | Leu | |
| | | 130 | | | | | 135 | | | | | 140 | | | | |
| gcc | acc | tgc | gcg | gcc | aag | tac | ggc | gac | gcc | cgc | gac | gcg | ctc | gcc | gcg | 600 |
| Ala | Thr | Cys | Ala | Ala | Lys | Tyr | Gly | Asp | Ala | Arg | Asp | Ala | Leu | Ala | Ala | |
| | 145 | | | | | 150 | | | | | 155 | | | | | |
| gcc | aag | ggc | tcg | atc | gcg | cag | cag | gac | tac | gac | atg | gcg | tcc | gtg | cac | 648 |
| Ala | Lys | Gly | Ser | Ile | Ala | Gln | Gln | Asp | Tyr | Asp | Met | Ala | Ser | Val | His | |
| 160 | | | | | 165 | | | | | 170 | | | | | 175 | |
| gtc | agc | gcc | gcc | gcg | gag | tac | ccg | cag | gtg | tgc | agg | acg | ctg | ttc | ggg | 696 |
| Val | Ser | Ala | Ala | Ala | Glu | Tyr | Pro | Gln | Val | Cys | Arg | Thr | Leu | Phe | Gly | |
| | | | 180 | | | | | 185 | | | | | 190 | | | |
| cgg | cag | agc | ccc | gga | gac | tac | ccg | ccg | gag | ctc | gcc | gcg | aca | gag | gtg | 744 |
| Arg | Gln | Ser | Pro | Gly | Asp | Tyr | Pro | Pro | Glu | Leu | Ala | Ala | Thr | Glu | Val | |
| | | 195 | | | | | 200 | | | | | 205 | | | | |
| gcg | ctc | agg | cag | ctc | tgc | tcc | gtc | gcg | ctc | gac | atc | atc | gcg | ctc | ctc | 792 |
| Ala | Leu | Arg | Gln | Leu | Cys | Ser | Val | Ala | Leu | Asp | Ile | Ile | Ala | Leu | Leu | |
| | | 210 | | | | | 215 | | | | | 220 | | | | |
| agc | tca | tcc | agc | aac | tag | cagctctgct tgttaccgag ctcaagttca | | | | | | | | | | 840 |
| Ser | Ser | Ser | Ser | Asn | * | | | | | | | | | | | |
| | | 225 | | | | | | | | | | | | | | |

```
cccaaccagc taactactcg caattcgtat aggtacaaat ggtgcaaata tagtactgta     900
taatactact gcatagaata catatacgtg taatgacacg tatttatctt ttttttttgc     960 aagggcacg tatatcaatt aattgtgtgt cccaattaat tagagtcgaa tccacttgat    1020
atgttctttt gttaatttgt attatcactc catagaggag ttgctgtagt agtgcaaaag   1080
gtacatgcgg ccgccggcag tatgcatgta tttcacttct gtttcagtat aataatggct   1140
attcaaaaaa aaaaaaaaaa aaaaaaaaaa aaaaaaaaaa aaaaaaaaaa aaaaaaaaa    1200
```
aaaaaaaaaa aaaa                                                                  1214

<210> SEQ ID NO 29
<211> LENGTH: 228
<212> TYPE: PRT
<213> ORGANISM: Oryza sativa

<400> SEQUENCE: 29

Met Ala Ser Met Ala Pro Ser Ala Met Val Leu Ile Val Leu Leu Val
1               5                   10                  15

Leu Val Val Leu Pro Ser Ser Thr Leu Cys Ser Arg Ala Gly Pro Ser
            20                  25                  30

Ser Lys His Gly His Gly Gly Gly His Ala Lys Arg Val Pro Pro Pro
        35                  40                  45

Ala Ser Val Pro Pro Pro Pro Pro Pro Ala Pro Ala Ala Leu
    50                  55                  60

Val Arg Ala Thr Cys Asn Ser Thr Ser Tyr Tyr Asp Leu Cys Val Ala
65                  70                  75                  80

Glu Leu Ser Ala Asp Pro Ser Ser Ala Thr Ala Asp Val Arg Gly Leu
                85                  90                  95

Ser Ser Ile Ala Val Ser Ala Ala Ala Asn Ala Ser Gly Ala Ala
            100                 105                 110

Gln Ala Ala Ser Ala Leu Ala Asn Ala Thr Asp Ala Gly Thr Thr Ala
        115                 120                 125

Gly Val Ala Gly Asp Gly Gly Ala Val Val Gln Arg Leu Leu Ala
    130                 135                 140

Thr Cys Ala Ala Lys Tyr Gly Asp Ala Arg Asp Ala Leu Ala Ala Ala
145                 150                 155                 160

Lys Gly Ser Ile Ala Gln Gln Asp Tyr Asp Met Ala Ser Val His Val
                165                 170                 175

Ser Ala Ala Glu Tyr Pro Gln Val Cys Arg Thr Leu Phe Gly Arg
            180                 185                 190

Gln Ser Pro Gly Asp Tyr Pro Pro Glu Leu Ala Ala Thr Glu Val Ala
        195                 200                 205

Leu Arg Gln Leu Cys Ser Val Ala Leu Asp Ile Ile Ala Leu Leu Ser
    210                 215                 220

Ser Ser Ser Asn
225

<210> SEQ ID NO 30
<211> LENGTH: 687
<212> TYPE: DNA
<213> ORGANISM: Oryza sativa

<400> SEQUENCE: 30
atggcatcaa tggcgccatc ggcaatggtg ctcatcgtcc tcctcgtcct ggtggttctc      60
ccgtcgagca ctctgtgctc acgggcgggg ccttcttcca agcacggcca tggcggtggc     120
cacgccaagc gcgtgccgcc accggcgtcg gtaccgccgc cgccgccgcc gccaccagcg     180
ccggcggcgc tggtgcgtgc cacctgcaac tccacctcct actacgacct ctgcgtcgcc     240
gagctgtccg ccgacccgtc gagcgccacg gccgacgtgc gcggactgtc gtccatcgcc     300
gtctccgccg ccgccgccaa cgcatccggg gcggcgcagg cggcctcggc gctggcgaac     360
gcgaccgacg cggggacgac ggcggggcgtc gccggcgacg gcggcggcgc agtcgtacag     420
aggctgctcg ccacctgcgc ggccaagtac ggcgacgccc gcgacgcgct cgccgcggcc     480

-continued

```
aagggctcga tcgcgcagca ggactacgac atggcgtccg tgcacgtcag cgccgccgcg      540
gagtacccgc aggtgtgcag gacgctgttc gggcggcaga gccccggaga ctacccgccg      600
gagctcgccg cgacagaggt ggcgctcagg cagctctgct ccgtcgcgct cgacatcatc      660
gcgctcctca gctcatccag caactag                                          687

<210> SEQ ID NO 31
<211> LENGTH: 782
<212> TYPE: DNA
<213> ORGANISM: Glycine max
<220> FEATURE:
<221> NAME/KEY: CDS
<222> LOCATION: (81)...(620)

<400> SEQUENCE: 31
attgtctcct ccctttcac ccctctcccc cctcaaaaaa tctcaagata ccaattagca       60
ccctcctata ctaatctata atg gct tct tct aag atc atc ttc ata ttt ctc     113
                         Met Ala Ser Ser Lys Ile Ile Phe Ile Phe Leu
                           1               5                      10 ctc ttt cta gca cac ctt cat caa cat aca ttt gtg aaa gga gat tcc       161
Leu Phe Leu Ala His Leu His Gln His Thr Phe Val Lys Gly Asp Ser
             15                  20                  25 agt ttg ata aag aga act tgc aag aac acc aag tac tac aat cta tgc       209
Ser Leu Ile Lys Arg Thr Cys Lys Asn Thr Lys Tyr Tyr Asn Leu Cys
         30                  35                  40 ttc tct tcc ctc aaa tct gat cct agc agt cca aac gca gat cct aag       257
Phe Ser Ser Leu Lys Ser Asp Pro Ser Ser Pro Asn Ala Asp Pro Lys
     45                  50                  55 ggc cta gct gtg atc atg att ggg att gga atg acc aat gcc act tcc       305
Gly Leu Ala Val Ile Met Ile Gly Ile Gly Met Thr Asn Ala Thr Ser
 60                  65                  70                  75 act tct tcc tac ttg tct tca aag ttg ctt agc ccc tcc aac aac aca       353
Thr Ser Ser Tyr Leu Ser Ser Lys Leu Leu Ser Pro Ser Asn Asn Thr
                 80                  85                  90 acc ttg aaa agg gtc cta aag gag tgt gca gat aag tac tca tat gct       401
Thr Leu Lys Arg Val Leu Lys Glu Cys Ala Asp Lys Tyr Ser Tyr Ala
             95                 100                 105 ggt gat gcc ctc caa gat tcg gtt cag gat ttg gct aat gag gct tat       449
Gly Asp Ala Leu Gln Asp Ser Val Gln Asp Leu Ala Asn Glu Ala Tyr
         110                 115                 120 gac tat gct tac atg cac atc act gcc gcc aaa gat tac cca aat gct       497
Asp Tyr Ala Tyr Met His Ile Thr Ala Ala Lys Asp Tyr Pro Asn Ala
     125                 130                 135 tgc cac aac gct ttc aaa cgg tac ccc ggt ttg gct tat cct cgt gat       545
Cys His Asn Ala Phe Lys Arg Tyr Pro Gly Leu Ala Tyr Pro Arg Asp
140                 145                 150                 155 ctt gct agt aga gaa gat ggt ttg aag cat ata tgt gat gtg gca atg       593
Leu Ala Ser Arg Glu Asp Gly Leu Lys His Ile Cys Asp Val Ala Met
                 160                 165                 170 ggg att ata gat aat ctt gat tgg tag gtgcatgcat ttgagtatat             640
Gly Ile Ile Asp Asn Leu Asp Trp *
             175 agcttccagt tgttgtgca aaccatgtta tatctctggt gttatgtttg gttactatgt      700 attgttaagt tcttggtata atatattaat gggaacaaaa ttttagtatt tgtttagaaa     760 aaaaaaaaaa aaaaaaaaa aa                                               782

<210> SEQ ID NO 32
<211> LENGTH: 179
<212> TYPE: PRT
```

<213> ORGANISM: Glycine max

<400> SEQUENCE: 32

```
Met Ala Ser Ser Lys Ile Ile Phe Ile Phe Leu Leu Phe Leu Ala His
 1               5                  10                  15
Leu His Gln His Thr Phe Val Lys Gly Asp Ser Ser Leu Ile Lys Arg
             20                  25                  30
Thr Cys Lys Asn Thr Lys Tyr Tyr Asn Leu Cys Phe Ser Ser Leu Lys
         35                  40                  45
Ser Asp Pro Ser Pro Asn Ala Asp Pro Lys Gly Leu Ala Val Ile
     50                  55                  60
Met Ile Gly Ile Gly Met Thr Asn Ala Thr Ser Thr Ser Ser Tyr Leu
 65                  70                  75                  80
Ser Ser Lys Leu Leu Ser Pro Ser Asn Asn Thr Thr Leu Lys Arg Val
                 85                  90                  95
Leu Lys Glu Cys Ala Asp Lys Tyr Ser Tyr Ala Gly Asp Ala Leu Gln
            100                 105                 110
Asp Ser Val Gln Asp Leu Ala Asn Glu Ala Tyr Asp Tyr Ala Tyr Met
            115                 120                 125
His Ile Thr Ala Ala Lys Asp Tyr Pro Asn Ala Cys His Asn Ala Phe
        130                 135                 140
Lys Arg Tyr Pro Gly Leu Ala Tyr Pro Arg Asp Leu Ala Ser Arg Glu
145                 150                 155                 160
Asp Gly Leu Lys His Ile Cys Asp Val Ala Met Gly Ile Ile Asp Asn
                165                 170                 175
Leu Asp Trp
```

<210> SEQ ID NO 33
<211> LENGTH: 540
<212> TYPE: DNA
<213> ORGANISM: Glycine max

<400> SEQUENCE: 33

```
atggcttctt ctaagatcat cttcatattt ctcctctttc tagcacacct tcatcaacat    60
acatttgtga aaggagattc cagtttgata aagagaactt gcaagaacac caagtactac   120
aatctatgct tctcttccct caaatctgat cctagcagtc caaacgcaga tcctaagggc   180
ctagctgtga tcatgattgg gattggaatg accaatgcca cttccacttc ttcctacttg   240
tcttcaaagt tgcttagccc ctccaacaac acaaccttga aagggtcct aaaggagtgt   300
gcagataagt actcatatgc tggtgatgcc ctccaagatt cggttcagga tttggctaat   360
gaggcttatg actatgctta catgcacatc actgccgcca agattacccc aaatgcttgc   420
cacaacgctt tcaaacggta ccccggtttg gcttatcctc gtgatcttgc tagtagagaa   480
gatggttga agcatatatg tgatgtggca atggggatta gataatct tgattggtag     540
```

<210> SEQ ID NO 34
<211> LENGTH: 814
<212> TYPE: DNA
<213> ORGANISM: Glycine max
<220> FEATURE:
<221> NAME/KEY: CDS
<222> LOCATION: (99)...(638)

<400> SEQUENCE: 34

```
gcccacattt tctatatact tttgaattgt cttctccctt ttcaccccct ctcccctcaa    60
aaaatctaaa gacacaaaac accctcctat actctata atg gtt tct tct aag atc   116
```

```
                         Met Val Ser Ser Lys Ile
                          1               5
ttc ttc ctt ttt ctc ctc ttt cta gca cac ctt cat caa cat gca tct    164
Phe Phe Leu Phe Leu Leu Phe Leu Ala His Leu His Gln His Ala Ser
             10                  15                  20 gtg gaa gga gat tcc agt ttg ata aag aga act tgc aag aac acc aag    212
Val Glu Gly Asp Ser Ser Leu Ile Lys Arg Thr Cys Lys Asn Thr Lys
         25                  30                  35 tac tac aat cta tgc ttc tct tcc ctc aaa tct gat cca agc agt cca    260
Tyr Tyr Asn Leu Cys Phe Ser Ser Leu Lys Ser Asp Pro Ser Ser Pro
     40                  45                  50 aac gca gat cct aag ggc cta gct gtg atc atg att gga ata gga atg    308
Asn Ala Asp Pro Lys Gly Leu Ala Val Ile Met Ile Gly Ile Gly Met
 55                  60                  65                  70 acc aat gcc act tcc aca tcc tcc tac ttg tct tca aag ttg cct acc    356
Thr Asn Ala Thr Ser Thr Ser Ser Tyr Leu Ser Ser Lys Leu Pro Thr
                 75                  80                  85 ccc tcc aac aac aca acc tgg aaa agg gtc ctc aag gag tgt gct gat    404
Pro Ser Asn Asn Thr Thr Trp Lys Arg Val Leu Lys Glu Cys Ala Asp
             90                  95                 100 aag tac tcc tat gct ggt gat gcc ctc caa gat tcg gtg cag gat ttg    452
Lys Tyr Ser Tyr Ala Gly Asp Ala Leu Gln Asp Ser Val Gln Asp Leu
         105                 110                 115 gct aat gag gct tat gac tat gct tac atg cac atc act gcc gcc aaa    500
Ala Asn Glu Ala Tyr Asp Tyr Ala Tyr Met His Ile Thr Ala Ala Lys
     120                 125                 130 gat tac cca aat gct tgc cac aac gct ttc aaa cgg tac cct ggt ttg    548
Asp Tyr Pro Asn Ala Cys His Asn Ala Phe Lys Arg Tyr Pro Gly Leu
135                 140                 145                 150 gtt tat cct cgt gat ctt gct cgt aga gaa gat ggt ttg aag cat ata    596
Val Tyr Pro Arg Asp Leu Ala Arg Arg Glu Asp Gly Leu Lys His Ile
                 155                 160                 165 tgc gat gtg gca atg ggg att ata gat aat ctt gat tgg tag            638
Cys Asp Val Ala Met Gly Ile Ile Asp Asn Leu Asp Trp *
             170                 175 gtgcatgcat ttgagtatat agcttccagt ttgttatgca aaccatgtta tatctctggt   698
gttatgtttg ctaccttgt atcttgttaa ttatgttctt ggtataatat attggacata    758
aatgttttag tctttttgaa aaaaaaaaaa aaaaaaaaaa aaaaaaaaaa aaaaaa        814
```

<210> SEQ ID NO 35
<211> LENGTH: 179
<212> TYPE: PRT
<213> ORGANISM: Glycine max

<400> SEQUENCE: 35

Met Val Ser Ser Lys Ile Phe Phe Leu Phe Leu Leu Phe Leu Ala His
 1               5                  10                  15

Leu His Gln His Ala Ser Val Glu Gly Asp Ser Ser Leu Ile Lys Arg
             20                  25                  30

Thr Cys Lys Asn Thr Lys Tyr Tyr Asn Leu Cys Phe Ser Ser Leu Lys
         35                  40                  45

Ser Asp Pro Ser Ser Pro Asn Ala Asp Pro Lys Gly Leu Ala Val Ile
     50                  55                  60

Met Ile Gly Ile Gly Met Thr Asn Ala Thr Ser Thr Ser Ser Tyr Leu
 65                  70                  75                  80

Ser Ser Lys Leu Pro Thr Pro Ser Asn Asn Thr Thr Trp Lys Arg Val
                 85                  90                  95

-continued

```
Leu Lys Glu Cys Ala Asp Lys Tyr Ser Tyr Ala Gly Asp Ala Leu Gln
            100                 105                 110
Asp Ser Val Gln Asp Leu Ala Asn Glu Ala Tyr Asp Tyr Ala Tyr Met
        115                 120                 125
His Ile Thr Ala Ala Lys Asp Tyr Pro Asn Ala Cys His Asn Ala Phe
    130                 135                 140
Lys Arg Tyr Pro Gly Leu Val Tyr Pro Arg Asp Leu Ala Arg Arg Glu
145                 150                 155                 160
Asp Gly Leu Lys His Ile Cys Asp Val Ala Met Gly Ile Ile Asp Asn
                165                 170                 175
Leu Asp Trp
```

<210> SEQ ID NO 36
<211> LENGTH: 540
<212> TYPE: DNA
<213> ORGANISM: Glycine max

<400> SEQUENCE: 36

```
atggtttctt ctaagatctt cttccttttt ctcctctttc tagcacacct tcatcaacat      60
gcatctgtgg aaggagattc cagtttgata aagagaactt gcaagaacac caagtactac     120
aatctatgct tctcttccct caaatctgat ccaagcagtc aaacgcaga tcctaagggc      180
ctagctgtga tcatgattgg aataggaatg accaatgcca cttccacatc ctcctacttg     240
tcttcaaagt tgcctacccc ctccaacaac acaacctgga aaagggtcct caaggagtgt     300
gctgataagt actcctatgc tggtgatgcc ctccaagatt cggtgcagga tttggctaat     360
gaggcttatg actatgctta catgcacatc actgccgcca agattaccc aaatgcttgc     420
cacaacgctt tcaaacggta ccctggtttg gtttatcctc gtgatcttgc tcgtagagaa     480
gatggtttga agcatatatg cgatgtggca atggggatta gataatctt tgattggtag     540
```

<210> SEQ ID NO 37
<211> LENGTH: 766
<212> TYPE: DNA
<213> ORGANISM: Glycine max
<220> FEATURE:
<221> NAME/KEY: CDS
<222> LOCATION: (6)...(542)

<400> SEQUENCE: 37

```
caaca atg aca aac ttg aag cct cta att ctc tta gcc att att gtt atg      50
      Met Thr Asn Leu Lys Pro Leu Ile Leu Leu Ala Ile Ile Val Met
        1               5                  10                  15 att tca ata cca tca agc cac tgc aga acc ttg ctt cca gaa aat gaa        98
Ile Ser Ile Pro Ser Ser His Cys Arg Thr Leu Leu Pro Glu Asn Glu
                 20                  25                  30 aag ctg ata gag aac act tgc agg aag acc ccc aac tac aac gtt tgc       146
Lys Leu Ile Glu Asn Thr Cys Arg Lys Thr Pro Asn Tyr Asn Val Cys
             35                  40                  45 ctt gag tct ctg aag gca agc cct ggg agc tcc agt gct gac gtc aca       194
Leu Glu Ser Leu Lys Ala Ser Pro Gly Ser Ser Ser Ala Asp Val Thr
         50                  55                  60 ggg cta gct caa atc atg gtg aaa gag atg aag gca aaa gca aac tat       242
Gly Leu Ala Gln Ile Met Val Lys Glu Met Lys Ala Lys Ala Asn Tyr
 65                  70                  75 gca ttg aag aga atc cag gag ctg cag agg gtg gga gca ggg cct aat       290
Ala Leu Lys Arg Ile Gln Glu Leu Gln Arg Val Gly Ala Gly Pro Asn
     80                  85                  90                  95 aag caa aga aga gcc ttg agt tct tgt gtt gat aaa tac aaa acg gtt       338
```

```
          Lys Gln Arg Arg Ala Leu Ser Ser Cys Val Asp Lys Tyr Lys Thr Val
                          100                 105                 110 tta att gct gat gtt cca caa gcc act gag gct ctg cag aaa ggg gac        386
Leu Ile Ala Asp Val Pro Gln Ala Thr Glu Ala Leu Gln Lys Gly Asp
            115                 120                 125 ccc aag ttt gct gaa gat ggg gct aat gat gct gct aat gag gct acc        434
Pro Lys Phe Ala Glu Asp Gly Ala Asn Asp Ala Ala Asn Glu Ala Thr
        130                 135                 140 ttt tgt gag gct gat ttc tct gct ggg aat tcc cca ctc acc aaa cag        482
Phe Cys Glu Ala Asp Phe Ser Ala Gly Asn Ser Pro Leu Thr Lys Gln
    145                 150                 155 aac aat gct atg cat gat gtt gct gct gtt act gcc gct att gtt aga        530
Asn Asn Ala Met His Asp Val Ala Ala Val Thr Ala Ala Ile Val Arg
160                 165                 170                 175 ttg ttg ctc taa taattctagt tgctgaaacc tatatatg cttaattgta              582
Leu Leu Leu * ttaactaaat atagattata gatgtctctg catcatgctg acttggtgcc tgttaactgt      642
aatgtgaaaa tactatcttt tttataaaat gttgttatat gtaataaaat ccaaccctct      702
cgtgattctc acgagtttcc cagaaaaaaa aaaaaaaaaa aaaaaaaaaa aaaaaaaaaa      762
aaaa                                                                   766

<210> SEQ ID NO 38
<211> LENGTH: 178
<212> TYPE: PRT
<213> ORGANISM: Glycine max

<400> SEQUENCE: 38

Met Thr Asn Leu Lys Pro Leu Ile Leu Ala Ile Ile Val Met Ile
 1               5                  10                  15

Ser Ile Pro Ser Ser His Cys Arg Thr Leu Leu Pro Glu Asn Glu Lys
                20                  25                  30

Leu Ile Glu Asn Thr Cys Arg Lys Thr Pro Asn Tyr Asn Val Cys Leu
            35                  40                  45

Glu Ser Leu Lys Ala Ser Pro Gly Ser Ser Ser Ala Asp Val Thr Gly
        50                  55                  60

Leu Ala Gln Ile Met Val Lys Glu Met Lys Ala Lys Ala Asn Tyr Ala
65                  70                  75                  80

Leu Lys Arg Ile Gln Glu Leu Gln Arg Val Gly Ala Gly Pro Asn Lys
                85                  90                  95

Gln Arg Arg Ala Leu Ser Ser Cys Val Asp Lys Tyr Lys Thr Val Leu
            100                 105                 110

Ile Ala Asp Val Pro Gln Ala Thr Glu Ala Leu Gln Lys Gly Asp Pro
        115                 120                 125

Lys Phe Ala Glu Asp Gly Ala Asn Asp Ala Ala Asn Glu Ala Thr Phe
    130                 135                 140

Cys Glu Ala Asp Phe Ser Ala Gly Asn Ser Pro Leu Thr Lys Gln Asn
145                 150                 155                 160

Asn Ala Met His Asp Val Ala Ala Val Thr Ala Ala Ile Val Arg Leu
                165                 170                 175

Leu Leu

<210> SEQ ID NO 39
<211> LENGTH: 537
<212> TYPE: DNA
<213> ORGANISM: Glycine max
```

-continued

```
<400> SEQUENCE: 39
atgacaaact tgaagcctct aattctctta gccattattg ttatgatttc ataccatca      60 agccactgca gaaccttgct tccagaaaat gaaaagctga tagagaacac ttgcaggaag    120
acccccaact acaacgtttg ccttgagtct ctgaaggcaa gccctgggag ctccagtgct    180
gacgtcacag gctagctca aatcatggtg aaagagatga aggcaaaagc aaactatgca     240
ttgaagagaa tccaggagct gcagagggtg ggagcagggc taataagca agaagagcc      300 ttgagttctt gtgttgataa atacaaaacg gttttaattg ctgatgttcc acaagccact    360
gaggctctgc agaaagggga ccccaagttt gctgaagatg gggctaatga tgctgctaat    420
gaggctacct tttgtgaggc tgatttctct gctgggaatt ccccactcac caaacagaac    480
aatgctatgc atgatgttgc tgctgttact gccgctattg ttagattgtt gctctaa      537

<210> SEQ ID NO 40
<211> LENGTH: 826
<212> TYPE: DNA
<213> ORGANISM: Glycine max
<220> FEATURE:
<221> NAME/KEY: CDS
<222> LOCATION: (111)...(719)
<221> NAME/KEY: misc_feature
<222> LOCATION: (1)...(826)
<223> OTHER INFORMATION: n = A,T,C or G

<400> SEQUENCE: 40
aaaaggttag gtccactaca tctgctccta accataaaaa ggcctagcag cattccattc      60
agtggaatct agcaactacc aaaaccaatc tctttcaata atcaacaaca atg aca         116
                                                         Met Thr
                                                           1 aac ttg aag cct cta att ctc ttc ttt tat ctc cta gcc att gtt gtt       164
Asn Leu Lys Pro Leu Ile Leu Phe Phe Tyr Leu Leu Ala Ile Val Val
        5                  10                  15 atg att tca ata cca tca agc cac tgc agc aga acc ttg ctt cca gaa       212
Met Ile Ser Ile Pro Ser Ser His Cys Ser Arg Thr Leu Leu Pro Glu
20                  25                  30 aac gaa aag ctg ata gag aac act tgc aag aaa act ccc aac tac aac       260
Asn Glu Lys Leu Ile Glu Asn Thr Cys Lys Lys Thr Pro Asn Tyr Asn
    35                  40                  45                  50 gtt tgc ctt gag tct ctg aag gca agc cct ggg agc tcc agt gct gac       308
Val Cys Leu Glu Ser Leu Lys Ala Ser Pro Gly Ser Ser Ser Ala Asp
                55                  60                  65 gtc aca ggg ctg gct caa atc atg gtc aaa gag atg aag gcc aaa gca       356
Val Thr Gly Leu Ala Gln Ile Met Val Lys Glu Met Lys Ala Lys Ala
            70                  75                  80 aac gat gca ttg aaa aga atc caa gag ttg cag agg gtg gga gca tcg       404
Asn Asp Ala Leu Lys Arg Ile Gln Glu Leu Gln Arg Val Gly Ala Ser
        85                  90                  95 ggg cct aag caa aga aga gcc ttg agt tct tgt gct gat aaa tac aaa       452
Gly Pro Lys Gln Arg Arg Ala Leu Ser Ser Cys Ala Asp Lys Tyr Lys
    100                 105                 110 gcg gtt tta att gct gat gtt cca caa gcc act gag gct ctg cag aaa       500
Ala Val Leu Ile Ala Asp Val Pro Gln Ala Thr Glu Ala Leu Gln Lys
115                 120                 125                 130 ggt gac ccc aag ttt gct gaa gat ggg gct aat gat gct gct aat gag       548
Gly Asp Pro Lys Phe Ala Glu Asp Gly Ala Asn Asp Ala Ala Asn Glu
                135                 140                 145 gct act tat tgt gag act gat ttc tct gca gca ggg aat tcc cca ctc       596
Ala Thr Tyr Cys Glu Thr Asp Phe Ser Ala Ala Gly Asn Ser Pro Leu
            150                 155                 160
```

```
acc aaa cag aac aat gct atg cat gat gtt gct gct gtt act gcc gct      644
Thr Lys Gln Asn Asn Ala Met His Asp Val Ala Ala Val Thr Ala Ala
        165                 170                 175 att gtt aaa ttg ttg ctc caa act ata tat act aaa ttg tac ctg tta      692
Ile Val Lys Leu Leu Leu Gln Thr Ile Tyr Thr Lys Leu Tyr Leu Leu
180                 185                 190 act gta atg gtg aaa ata cta tcc taa ttttaaaagc ctttttata             739
Thr Val Met Val Lys Ile Leu Ser *
195                 200 aaaatngttt attaatatgt taataaaaat ccaaaccctc cccgtngaat tctcaacaaa    799
tttcccaaaa aaaaaaaaaa aaaaaaa                                        826

<210> SEQ ID NO 41
<211> LENGTH: 202
<212> TYPE: PRT
<213> ORGANISM: Glycine max

<400> SEQUENCE: 41

Met Thr Asn Leu Lys Pro Leu Ile Leu Phe Phe Tyr Leu Leu Ala Ile
1               5                   10                  15

Val Val Met Ile Ser Ile Pro Ser Ser His Cys Ser Arg Thr Leu Leu
            20                  25                  30

Pro Glu Asn Glu Lys Leu Ile Glu Asn Thr Cys Lys Lys Thr Pro Asn
        35                  40                  45

Tyr Asn Val Cys Leu Glu Ser Leu Lys Ala Ser Pro Gly Ser Ser Ser
    50                  55                  60

Ala Asp Val Thr Gly Leu Ala Gln Ile Met Val Lys Glu Met Lys Ala
65                  70                  75                  80

Lys Ala Asn Asp Ala Leu Lys Arg Ile Gln Glu Leu Gln Arg Val Gly
                85                  90                  95

Ala Ser Gly Pro Lys Gln Arg Arg Ala Leu Ser Ser Cys Ala Asp Lys
            100                 105                 110

Tyr Lys Ala Val Leu Ile Ala Asp Val Pro Gln Ala Thr Glu Ala Leu
        115                 120                 125

Gln Lys Gly Asp Pro Lys Phe Ala Glu Asp Gly Ala Asn Asp Ala Ala
    130                 135                 140

Asn Glu Ala Thr Tyr Cys Glu Thr Asp Phe Ser Ala Ala Gly Asn Ser
145                 150                 155                 160

Pro Leu Thr Lys Gln Asn Asn Ala Met His Asp Val Ala Ala Val Thr
                165                 170                 175

Ala Ala Ile Val Lys Leu Leu Leu Gln Thr Ile Tyr Thr Lys Leu Tyr
            180                 185                 190

Leu Leu Thr Val Met Val Lys Ile Leu Ser
        195                 200

<210> SEQ ID NO 42
<211> LENGTH: 609
<212> TYPE: DNA
<213> ORGANISM: Glycine max

<400> SEQUENCE: 42
atgacaaact tgaagcctct aattctcttc ttttatctcc tagccattgt tgttatgatt      60
tcaataccat caagccactg cagcagaacc ttgcttccag aaaacgaaaa gctgatagag     120
aacacttgca agaaaactcc caactacaac gtttgccttg agtctctgaa ggcaagccct     180
gggagctcca gtgctgacgt cacagggctg gctcaaatca tggtcaaaga gatgaaggcc     240
```

```
aaagcaaacg atgcattgaa aagaatccaa gagttgcaga gggtgggagc atcggggcct    300
aagcaaagaa gagccttgag ttcttgtgct gataaataca aagcggtttt aattgctgat    360
gttccacaag ccactgaggc tctgcagaaa ggtgacccca gtttgctga agatgggct     420 aatgatgctg ctaatgaggc tacttattgt gagactgatt tctctgcagc agggaattcc    480
ccactcacca aacagaacaa tgctatgcat gatgttgctg ctgttactgc cgctattgtt    540
aaattgttgc tccaaactat atatactaaa ttgtacctgt taactgtaat ggtgaaaata    600
ctatcctaa                                                           609

<210> SEQ ID NO 43
<211> LENGTH: 983
<212> TYPE: DNA
<213> ORGANISM: Glycine max
<220> FEATURE:
<221> NAME/KEY: CDS
<222> LOCATION: (50)...(598)

<400> SEQUENCE: 43
ccttcttcat cttctacttc tatctcccta catactcatt caaacagac atg aaa att     58
                                                    Met Lys Ile
                                                     1 atg gaa tca tta gct ctt atc ttc tac agt act ctt gtt tta gct acg    106
Met Glu Ser Leu Ala Leu Ile Phe Tyr Ser Thr Leu Val Leu Ala Thr
 5                  10                  15 att tca gtt cca gca act aac tcc aga atc atc cat caa aaa aac aat    154
Ile Ser Val Pro Ala Thr Asn Ser Arg Ile Ile His Gln Lys Asn Asn
 20                  25                  30                  35 gcc aat ctg att gaa gaa act tgc aag cag aca ccc cat cac gac ctt    202
Ala Asn Leu Ile Glu Glu Thr Cys Lys Gln Thr Pro His His Asp Leu
             40                  45                  50 tgc atc caa tac ctc tcc tcc gac cct cgc agc acc gaa gca gat gtg    250
Cys Ile Gln Tyr Leu Ser Ser Asp Pro Arg Ser Thr Glu Ala Asp Val
         55                  60                  65 aca ggg ctg gca ctt att atg gtc aac gta atc aaa atc aaa gca aac    298
Thr Gly Leu Ala Leu Ile Met Val Asn Val Ile Lys Ile Lys Ala Asn
     70                  75                  80 aat gca ttg gac aaa atc cac caa ctg ctt cag aaa aac cct gaa cct    346
Asn Ala Leu Asp Lys Ile His Gln Leu Leu Gln Lys Asn Pro Glu Pro
 85                  90                  95 agt caa aag gaa cca ctg agt tcg tgt gct gct aga tac aaa gca att    394
Ser Gln Lys Glu Pro Leu Ser Ser Cys Ala Ala Arg Tyr Lys Ala Ile
100                 105                 110                 115 gtg gaa gct gac gtg gca caa gcc gtt gcg tct ctg cag aaa gga gac    442
Val Glu Ala Asp Val Ala Gln Ala Val Ala Ser Leu Gln Lys Gly Asp
                 120                 125                 130 ccc aag ttc gca gaa gat ggt gcc aat gat gct gct att gag gcc acc    490
Pro Lys Phe Ala Glu Asp Gly Ala Asn Asp Ala Ala Ile Glu Ala Thr
             135                 140                 145 act tgt gag aac agc ttc tct gct ggg aaa tcg cca ctc acc aat cac    538
Thr Cys Glu Asn Ser Phe Ser Ala Gly Lys Ser Pro Leu Thr Asn His
         150                 155                 160 aac aat gct atg cac gat gtt gca acc ata act gca gct ata gtt aga    586
Asn Asn Ala Met His Asp Val Ala Thr Ile Thr Ala Ala Ile Val Arg
     165                 170                 175 caa ttg ctc tag tgacacttac tccaacggag gggatgatgc aatttaattt        638
Gln Leu Leu *
180 tcgtaatatc acattataat tatattttca attaacacaa cataaaatct tgctctcttg   698
```

-continued

```
ttggtctctt ctgtaatgga acacaactg cttttgccac ttcacaattc tcatttctca    758
ctgtcccctc tcctctgctt tccacgtttc ttattttcat ttttcttctt tgattcttgg    818
aaaataattg acagcgcatg ggatgtgata tgcctctgtc ttgtgcttct actttcttct    878
aatgtatcat caatttagcc tttttaactt taacaaacat ttgttaatca gatccttcat    938
attatgaaga tattgacatt taaacttaaa aaaaaaaaa aaaaa                     983
```

<210> SEQ ID NO 44
<211> LENGTH: 182
<212> TYPE: PRT
<213> ORGANISM: Glycine max

<400> SEQUENCE: 44

```
Met Lys Ile Met Glu Ser Leu Ala Leu Ile Phe Tyr Ser Thr Leu Val
 1               5                  10                  15

Leu Ala Thr Ile Ser Val Pro Ala Thr Asn Ser Arg Ile Ile His Gln
                20                  25                  30

Lys Asn Ala Asn Leu Ile Glu Glu Thr Cys Lys Gln Thr Pro His
         35                  40                  45

His Asp Leu Cys Ile Gln Tyr Leu Ser Ser Asp Pro Arg Ser Thr Glu
 50                  55                  60

Ala Asp Val Thr Gly Leu Ala Leu Ile Met Val Asn Val Ile Lys Ile
 65                  70                  75                  80

Lys Ala Asn Asn Ala Leu Asp Lys Ile His Gln Leu Leu Gln Lys Asn
                 85                  90                  95

Pro Glu Pro Ser Gln Lys Glu Pro Leu Ser Ser Cys Ala Ala Arg Tyr
            100                 105                 110

Lys Ala Ile Val Glu Ala Asp Val Ala Gln Ala Val Ala Ser Leu Gln
        115                 120                 125

Lys Gly Asp Pro Lys Phe Ala Glu Asp Gly Ala Asn Asp Ala Ala Ile
    130                 135                 140

Glu Ala Thr Thr Cys Glu Asn Ser Phe Ser Ala Gly Lys Ser Pro Leu
145                 150                 155                 160

Thr Asn His Asn Asn Ala Met His Asp Val Ala Thr Ile Thr Ala Ala
                165                 170                 175

Ile Val Arg Gln Leu Leu
            180
```

<210> SEQ ID NO 45
<211> LENGTH: 549
<212> TYPE: DNA
<213> ORGANISM: Glycine max

<400> SEQUENCE: 45

```
atgaaaatta tggaatcatt agctcttatc ttctacagta ctcttgtttt agctacgatt     60
tcagttccag caactaactc cagaatcatc catcaaaaaa acaatgccaa tctgattgaa    120
gaaacttgca agcagacacc ccatcacgac ctttgcatcc aatacctctc tccgaccct    180 cgcagcaccg aagcagatgt gacagggctg gcacttatta tggtcaacgt aatcaaaatc    240
aaagcaaaca atgcattgga caaatccac caactgcttc agaaaaaccc tgaacctagt    300
caaaaggaac cactgagttc gtgtgctgct agatacaaag caattgtgga agctgacgtg    360
gcacaagccg ttgcgtctct gcagaaagga gaccccaagt tcgcagaaga tggtgccaat    420
gatgctgcta ttgaggccac cacttgtgag aacagcttct ctgctgggaa atcgccactc    480
```

```
accaatcaca acaatgctat gcacgatgtt gcaaccataa ctgcagctat agttagacaa      540
ttgctctag                                                              549

<210> SEQ ID NO 46
<211> LENGTH: 609
<212> TYPE: DNA
<213> ORGANISM: Glycine max
<220> FEATURE:
<221> NAME/KEY: CDS
<222> LOCATION: (16)...(609)

<400> SEQUENCE: 46
gtttatacca aataa atg atg tta caa gct tct ttt ttg cgc ttg atc tct        51
              Met Met Leu Gln Ala Ser Phe Leu Arg Leu Ile Ser
                1               5                  10 ttc ttc ttt ctc atc gca ctc cct ctt gga aga agc tct acc acc ttg        99
Phe Phe Phe Leu Ile Ala Leu Pro Leu Gly Arg Ser Ser Thr Thr Leu
         15                  20                  25 aat gta cca aag gac ata atc aac caa aca tgc caa aaa tgt gcc aac       147
Asn Val Pro Lys Asp Ile Ile Asn Gln Thr Cys Gln Lys Cys Ala Asn
 30                  35                  40 caa tcc atc atc ttg agc tac aag cta tgc tcc act tct ctt ccg acg       195
Gln Ser Ile Ile Leu Ser Tyr Lys Leu Cys Ser Thr Ser Leu Pro Thr
 45                  50                  55                  60 gtt ccg gtg agt cac tcc gca aat ctc gaa ggg ttg gcg ttg gtt gca       243
Val Pro Val Ser His Ser Ala Asn Leu Glu Gly Leu Ala Leu Val Ala
                 65                  70                  75 atg gag cta gca cta gag aat gtc act agc act ttg gca atc ata gag       291
Met Glu Leu Ala Leu Glu Asn Val Thr Ser Thr Leu Ala Ile Ile Glu
             80                  85                  90 aag cta tta gat agc aca agt ttg gat aat tct gct ttg ggg tgc tta       339
Lys Leu Leu Asp Ser Thr Ser Leu Asp Asn Ser Ala Leu Gly Cys Leu
         95                 100                 105 gca gat tgc ttg gaa ctg tac tct gat gca gca tgg aca ata ctg aat       387
Ala Asp Cys Leu Glu Leu Tyr Ser Asp Ala Ala Trp Thr Ile Leu Asn
110                 115                 120 tcc gta ggt gtt ttc ttg tct ggg aat tat gat gta act agg att tgg       435
Ser Val Gly Val Phe Leu Ser Gly Asn Tyr Asp Val Thr Arg Ile Trp
125                 130                 135                 140 atg agt tca gtt atg gaa gca gca tca aca tgc caa caa ggt ttt act       483
Met Ser Ser Val Met Glu Ala Ala Ser Thr Cys Gln Gln Gly Phe Thr
                145                 150                 155 gag aga ggt gaa gct tct cct ttg aca cag gag aat tat aat ctc ttt       531
Glu Arg Gly Glu Ala Ser Pro Leu Thr Gln Glu Asn Tyr Asn Leu Phe
            160                 165                 170 cag ttg tgt ggt att gca ctt tgc att att cat ttg gct aca cct gga       579
Gln Leu Cys Gly Ile Ala Leu Cys Ile Ile His Leu Ala Thr Pro Gly
        175                 180                 185 gta cct tat tct caa tta ttc cac aga taa                               609
Val Pro Tyr Ser Gln Leu Phe His Arg *
    190                 195

<210> SEQ ID NO 47
<211> LENGTH: 197
<212> TYPE: PRT
<213> ORGANISM: Glycine max

<400> SEQUENCE: 47

Met Met Leu Gln Ala Ser Phe Leu Arg Leu Ile Ser Phe Phe Phe Leu
  1               5                  10                  15

Ile Ala Leu Pro Leu Gly Arg Ser Ser Thr Thr Leu Asn Val Pro Lys
```

```
                     20                  25                  30
Asp Ile Ile Asn Gln Thr Cys Gln Lys Cys Ala Asn Gln Ser Ile Ile
             35                  40                  45

Leu Ser Tyr Lys Leu Cys Ser Thr Ser Leu Pro Thr Val Pro Val Ser
     50                  55                  60

His Ser Ala Asn Leu Glu Gly Leu Ala Leu Val Ala Met Glu Leu Ala
 65                  70                  75                  80

Leu Glu Asn Val Thr Ser Thr Leu Ala Ile Ile Glu Lys Leu Leu Asp
                 85                  90                  95

Ser Thr Ser Leu Asp Asn Ser Ala Leu Gly Cys Leu Ala Asp Cys Leu
             100                 105                 110

Glu Leu Tyr Ser Asp Ala Ala Trp Thr Ile Leu Asn Ser Val Gly Val
         115                 120                 125

Phe Leu Ser Gly Asn Tyr Asp Val Thr Arg Ile Trp Met Ser Ser Val
     130                 135                 140

Met Glu Ala Ala Ser Thr Cys Gln Gln Gly Phe Thr Glu Arg Gly Glu
145                 150                 155                 160

Ala Ser Pro Leu Thr Gln Glu Asn Tyr Asn Leu Phe Gln Leu Cys Gly
                165                 170                 175

Ile Ala Leu Cys Ile Ile His Leu Ala Thr Pro Gly Val Pro Tyr Ser
            180                 185                 190

Gln Leu Phe His Arg
        195

<210> SEQ ID NO 48
<211> LENGTH: 594
<212> TYPE: DNA
<213> ORGANISM: Glycine max

<400> SEQUENCE: 48
atgatgttac aagcttcttt tttgcgcttg atctctttct tctttctcat cgcactccct    60
cttggaagaa gctctaccac cttgaatgta ccaaaggaca taatcaacca acatgccaa    120 aaatgtgcca accaatccat catcttgagc tacaagctat gctccacttc tcttccgacg    180
gttccggtga gtcactccgc aaatctcgaa gggttggcgt tggttgcaat ggagctagca    240
ctagagaatg tcactagcac tttggcaatc atagagaagc tattagatag cacaagtttg    300
gataattctg cttttggggtg cttagcagat tgcttggaac tgtactctga tgcagcatgg    360
acaatactga attccgtagg tgttttcttg tctgggaatt atgatgtaac taggatttgg    420
atgagttcag ttatggaagc agcatcaaca tgccaacaag gttttactga gagaggtgaa    480
gcttctcctt tgacacagga gaattataat ctctttcagt tgtgtggtat tgcactttgc    540
attattcatt tggctacacc tggagtacct tattctcaat tattccacag ataa          594

<210> SEQ ID NO 49
<211> LENGTH: 673
<212> TYPE: DNA
<213> ORGANISM: Triticum 1
<220> FEATURE:
<221> NAME/KEY: CDS
<222> LOCATION: (33)...(551)

<400> SEQUENCE: 49
cagaaacaca agaaaatcgt tgtagcaaag cc atg agg cca tca caa gct ctc    53
                                   Met Arg Pro Ser Gln Ala Leu
                                     1               5 tcg ctt ctc gtt gtt gtc ctc ctc ctc gtc tcg tcc agt gct tcc atc    101
```

```
Ser Leu Leu Val Val Leu Leu Val Ser Ser Ala Ser Ile
         10              15              20 cta gaa gat acc tgc aag cgc ttc gac ggc gct gac atc tat gat atc    149
Leu Glu Asp Thr Cys Lys Arg Phe Asp Gly Ala Asp Ile Tyr Asp Ile
     25              30              35 tgc atc aag ttc ttc aag gcc aac aag gac agc gcc acc aca gac aag    197
Cys Ile Lys Phe Phe Lys Ala Asn Lys Asp Ser Ala Thr Thr Asp Lys
 40              45              50              55 cgt ggc ctt gct gtc att gcc act aag att gcc agt gcg aca gct gtg    245
Arg Gly Leu Ala Val Ile Ala Thr Lys Ile Ala Ser Ala Thr Ala Val
             60              65              70 gac acc cgc aag cgc att gcc atc ctg aag gcc gag gaa aag gac cat    293
Asp Thr Arg Lys Arg Ile Ala Ile Leu Lys Ala Glu Glu Lys Asp His
         75              80              85 atg atc caa cag gtc ctc gcc tac tgt gac aat atg tac tcc aga gct    341
Met Ile Gln Gln Val Leu Ala Tyr Cys Asp Asn Met Tyr Ser Arg Ala
     90              95              100 atg ggc ttg ttt gac aaa gct gcc agg ggc atc ttg tca ggc agg ttg    389
Met Gly Leu Phe Asp Lys Ala Ala Arg Gly Ile Leu Ser Gly Arg Leu
105              110              115 ggc gac gcg gtg acg agc ctc agc tcc gcg ttg gat att ccc aaa tat    437
Gly Asp Ala Val Thr Ser Leu Ser Ser Ala Leu Asp Ile Pro Lys Tyr
120              125              130              135 tgc gat gac gag ttc ctc gag gca ggc gtg aag tca ccg ttc gat gcc    485
Cys Asp Asp Glu Phe Leu Glu Ala Gly Val Lys Ser Pro Phe Asp Ala
             140              145              150 gag aac agc gag ttc gag atg caa tgt gcc ata act ctg ggt gta acg    533
Glu Asn Ser Glu Phe Glu Met Gln Cys Ala Ile Thr Leu Gly Val Thr
         155              160              165 aag atg ctg acc ttc tag ttagctagcc agcgaggata tgaatctagg           581
Lys Met Leu Thr Phe  *
             170 taactacaac aagattccat agtaattttg atgagcaaac tcctcaaaat taataagccc  641 acaatgttat cactgaaaaa aaaaaaaaaa aa                                673

<210> SEQ ID NO 50
<211> LENGTH: 172
<212> TYPE: PRT
<213> ORGANISM: Triticum 1

<400> SEQUENCE: 50

Met Arg Pro Ser Gln Ala Leu Ser Leu Leu Val Val Leu Leu Leu
 1               5                  10                  15

Val Ser Ser Ala Ser Ile Leu Glu Asp Thr Cys Lys Arg Phe Asp
             20              25              30

Gly Ala Asp Ile Tyr Asp Ile Cys Ile Lys Phe Phe Lys Ala Asn Lys
             35              40              45

Asp Ser Ala Thr Thr Asp Lys Arg Gly Leu Ala Val Ile Ala Thr Lys
 50              55              60

Ile Ala Ser Ala Thr Ala Val Asp Thr Arg Lys Arg Ile Ala Ile Leu
65              70              75              80

Lys Ala Glu Glu Lys Asp His Met Ile Gln Gln Val Leu Ala Tyr Cys
             85              90              95

Asp Asn Met Tyr Ser Arg Ala Met Gly Leu Phe Asp Lys Ala Ala Arg
             100             105             110

Gly Ile Leu Ser Gly Arg Leu Gly Asp Ala Val Thr Ser Leu Ser Ser
         115             120             125
```

```
Ala Leu Asp Ile Pro Lys Tyr Cys Asp Asp Glu Phe Leu Glu Ala Gly
        130                 135                 140

Val Lys Ser Pro Phe Asp Ala Glu Asn Ser Glu Phe Glu Met Gln Cys
145                 150                 155                 160

Ala Ile Thr Leu Gly Val Thr Lys Met Leu Thr Phe
                165                 170
```

<210> SEQ ID NO 51
<211> LENGTH: 519
<212> TYPE: DNA
<213> ORGANISM: Triticum l

<400> SEQUENCE: 51

| | |
|---|---|
| atgaggccat cacaagctct ctcgcttctc gttgttgtcc tcctcctcgt ctcgtccagt | 60 |
| gcttccatcc tagaagatac ctgcaagcgc ttcgacggcg ctgacatcta tgatatctgc | 120 |
| atcaagttct tcaaggccaa caaggacagc gccaccacag acaagcgtgg ccttgctgtc | 180 |
| attgccacta agattgccag tgcgacagct gtggacaccc gcaagcgcat tgccatcctg | 240 |
| aaggccgagg aaaaggacca tatgatccaa caggtcctcg cctactgtga caatatgtac | 300 |
| tccagagcta tgggcttgtt tgacaaagct gccaggggca tcttgtcagg caggttgggc | 360 |
| gacgcggtga cgagcctcag ctccgcgttg gatattccca aatattgcga tgacgagttc | 420 |
| ctcgaggcag gcgtgaagtc accgttcgat gccgagaaca gcgagttcga gatgcaatgt | 480 |
| gccataactc tgggtgtaac gaagatgctg accttctag | 519 |

<210> SEQ ID NO 52
<211> LENGTH: 665
<212> TYPE: DNA
<213> ORGANISM: Triticum l.
<220> FEATURE:
<221> NAME/KEY: CDS
<222> LOCATION: (33)...(551)

<400> SEQUENCE: 52

```
cagaaacaca agaaaattgt tgcggcaaaa cc atg agg tcg ccg caa gct ctc          53
                                   Met Arg Ser Pro Gln Ala Leu
                                    1               5 tcg ctt ctt gtt gtt gtc ctc ctc ctt gcc tcg tcc agt gct tcc gtc         101
Ser Leu Leu Val Val Val Leu Leu Leu Ala Ser Ser Ser Ala Ser Val
            10                  15                  20 ata gaa gac aca tgc agg cgc ttc gat ggt gct gac atc tac gat atc         149
Ile Glu Asp Thr Cys Arg Arg Phe Asp Gly Ala Asp Ile Tyr Asp Ile
        25                  30                  35 tgc atc aag ttc ttc aag gcc aac aag gat agc gcc acc acg gac aag         197
Cys Ile Lys Phe Phe Lys Ala Asn Lys Asp Ser Ala Thr Thr Asp Lys
40                  45                  50                  55 cgt ggc ctt gct gtc atc gcc att ggg att gcc agt gcg aca gct gtg         245
Arg Gly Leu Ala Val Ile Ala Ile Gly Ile Ala Ser Ala Thr Ala Val
                60                  65                  70 gac acc cgc aag cgc gtc gcc acc ctg aag gcc gag gaa aag gat caa         293
Asp Thr Arg Lys Arg Val Ala Thr Leu Lys Ala Glu Glu Lys Asp Gln
        75                  80                  85 att atc cag cat gtc ctc gcc tac tgt gac aat atg tac tcc agt gtt         341
Ile Ile Gln His Val Leu Ala Tyr Cys Asp Asn Met Tyr Ser Ser Val
        90                  95                  100 gtg ggc cta ttt gac aag gct gcc agg ggc atc tcg ttg ggc agg ttg         389
Val Gly Leu Phe Asp Lys Ala Ala Arg Gly Ile Ser Leu Gly Arg Leu
    105                 110                 115 ggc gac gca gtg acg agc ctc agc tcc gca ctg gac att ccc aaa tat         437
```

```
Gly Asp Ala Val Thr Ser Leu Ser Ser Ala Leu Asp Ile Pro Lys Tyr
120                 125                 130                 135 tgc gat gac aag ttc ctc gag gca ggc gtg aag tcg cca ttc gat gcc         485
Cys Asp Asp Lys Phe Leu Glu Ala Gly Val Lys Ser Pro Phe Asp Ala
                140                 145                 150 gag aac agc gag ttc gag gtg caa tgt gca atc act ctg ggt gta acg         533
Glu Asn Ser Glu Phe Glu Val Gln Cys Ala Ile Thr Leu Gly Val Thr
                155                 160                 165 aag atg ctg acc atg tag ttagcgagtc ggcgaggaca tgaatgtggg                581
Lys Met Leu Thr Met  *
            170 aaactacaat aagagtccat agtaatttcg atgagtaaac tcctcaaaat taataagccc       641 acaaaaaaaa aaaaaaaaaa aaaa                                              665
```

<210> SEQ ID NO 53
<211> LENGTH: 172
<212> TYPE: PRT
<213> ORGANISM: Triticum l.

<400> SEQUENCE: 53

```
Met Arg Ser Pro Gln Ala Leu Ser Leu Leu Val Val Leu Leu Leu
1               5                   10                  15

Ala Ser Ser Ala Ser Val Ile Glu Asp Thr Cys Arg Arg Phe Asp
                20                  25                  30

Gly Ala Asp Ile Tyr Asp Ile Cys Ile Lys Phe Phe Lys Ala Asn Lys
                35                  40                  45

Asp Ser Ala Thr Thr Asp Lys Arg Gly Leu Ala Val Ile Ala Ile Gly
                50                  55                  60

Ile Ala Ser Ala Thr Ala Val Asp Thr Arg Lys Arg Val Ala Thr Leu
65                  70                  75                  80

Lys Ala Glu Glu Lys Asp Gln Ile Ile Gln His Val Leu Ala Tyr Cys
                85                  90                  95

Asp Asn Met Tyr Ser Ser Val Val Gly Leu Phe Asp Lys Ala Ala Arg
                100                 105                 110

Gly Ile Ser Leu Gly Arg Leu Gly Asp Ala Val Thr Ser Leu Ser Ser
                115                 120                 125

Ala Leu Asp Ile Pro Lys Tyr Cys Asp Asp Lys Phe Leu Glu Ala Gly
                130                 135                 140

Val Lys Ser Pro Phe Asp Ala Glu Asn Ser Glu Phe Glu Val Gln Cys
145                 150                 155                 160

Ala Ile Thr Leu Gly Val Thr Lys Met Leu Thr Met
                165                 170
```

<210> SEQ ID NO 54
<211> LENGTH: 519
<212> TYPE: DNA
<213> ORGANISM: Triticum l.

<400> SEQUENCE: 54

```
atgaggtcgc cgcaagctct ctcgcttctt gttgttgtcc tcctccttgc ctcgtccagt        60
gcttccgtca tagaagacac atgcaggcgc ttcgatggtg ctgacatcta cgatatctgc       120
atcaagttct tcaaggccaa caaggatagc gccaccacgg acaagcgtgg ccttgctgtc       180
atcgccattg ggattgccag tgcgacagct gtggacaccc gcaagcgcgt cgccaccctg       240
aaggccgagg aaaaggatca aattatccag catgtcctcg cctactgtga caatatgtac       300
tccagtgttg tgggcctatt tgacaaggct gccaggggca tctcgttggg caggttgggc       360
```

-continued

```
gacgcagtga cgagcctcag ctccgcactg gacattccca aatattgcga tgacaagttc    420
ctcgaggcag gcgtgaagtc gccattcgat gccgagaaca gcgagttcga ggtgcaatgt    480
gcaatcactc tgggtgtaac gaagatgctg accatgtag                           519
```

INVERTASE INHIBITORS AND METHODS OF USE

CROSS-REFERENCE TO RELATED APPLICATIONS

This application claims the benefit of U.S. Provisional No. 60/181,509, filed Feb. 10, 2000.

FIELD OF THE INVENTION

The invention is drawn to the genetic modification of plants, particularly to the ablation of invertase inhibitor function to maintain female fertility.

BACKGROUND OF THE INVENTION

In cereals, water deficits can disrupt reproductive development and induce large yield reductions. In fact, the shortage of water during pollination increases the frequence of kernel abortion in maize (Westgate & Boyer (1986) *Crop Sci.* 26:951). The effects of water deficit are also seen around anthesis which also affects grain number (Schussler & Westgate (1991) *Crop Sci.* 31:1196). The losses around anthesis have been variously attributed to abnormal embryo-sac development or decreased silk receptivity depending upon when the water deficit occurs.

Low water potential inhibits dry matter accumulation and increases the concentration of assimilates in reproductive tissues (Zinselmeier et al. (1995) *Plant Physiol.* 107:385). Leaf water potentials decrease as water deficits develop, and photosynthesis is inhibited at the low water potentials causing embryo abortion. It has been demonstrated that by infusing a modified tissue culture medium into the stems and maintaining the supply of carbohydrate in addition to amino acids, basal salts, plant growth regulators, vitamins, and myo-inositol, early reproductive development could be sustained (Boyle et al. (1991) *Crop Sci.* 31:1246).

Under conditions of adequate water, maize ovaries accumulate starch during pollination and early kernel growth. The partitioning into starch reserves depends on assimilate supply as well as demand. At low water potential, starch levels in the reproductive shoot decrease indicating that assimilate supply is not sufficient to meet demand in the reproductive tissues of water-deficient plants.

Sucrose is the predominate sugar in higher plants. It serves several important functions, including acting as the major carbohydrate transport form, as a storage compound, and as an osmoprotectant. Higher plants metabolize sucrose either by sucrose synthase or by invertases (Greiner et al. (1998) *Plant Physiol.* 116:733). Plant invertases are located in the vacuole, the cytoplasm, and the cell wall. These different invertase isoenzymes each have specific functions requiring independent regulation. Several invertase isoforms have been cloned and their expression studied with respect to developmental regulation and tissue or cell-preferred expression (Cheng et al (1996) *Plant Cell* 8:971; Weber et al. (1995) *Plant Cell* 7:1835).

Because stress can have deleterious effects on plant growth and yield, methods are needed to increase yield in plants, particularly under stress conditions.

SUMMARY OF THE INVENTION

Methods and compositions for increasing yield in plants, particularly seed plants, are provided. The compositions comprise novel nucleic acid molecules encoding invertase inhibitors, antisense nucleotides corresponding to invertase inhibitors, and variants and fragments thereof. Such compositions find use in methods to modulate invertase activity in plants. The compositions are also useful in methods to modulate kernel development and for protecting plants against the harmful/detrimental effects of stress and adverse environmental conditions. The nucleotide sequences may be provided in constructs for temporal, developmental, and tissue preference.

Transformed plants, plant cells, tissues, and seeds are additionally provided.

BRIEF DESCRIPTION OF THE DRAWINGS

FIG. 1A indicates that with increasing quantity of inhibitor, invertase activity decreases. FIG. 1B indicates that sucrose ameliorates the effect of invertase inhibitor on maize invertase.

DETAILED DESCRIPTION OF THE INVENTION

Compositions and methods for modulating invertase function in plants are provided. The compositions comprise nucleotide sequences encoding invertase inhibitors, variants and fragments thereof. Nucleotide sequences of the invention also comprise complementary sequences for the invertase inhibitor genes. Particularly, a maize invertase inhibitor is provided.

Generally, the identification of a maize invertase inhibitor from early kernel tissues suggests that it may modulate kernel development in response to a continuing carbohydrate supply. Both the cell wall invertase and its corresponding invertase inhibitor may be co-expressed in early developing kernels. In the presence of sucrose to support early kernel development, the invertase inhibitor remains inactive. Thus, the invertase acts to supply the kernel with glucose and fructose. In instances where there is an inefficient amount of sucrose, the invertase inhibitor becomes active and inhibits the invertase activity resulting in kernel abortion. Thus, stress and transient decreases in sucrose result in irretrievable losses in yield.

The present invention provides a means for inactivating the activity of the invertase inhibitor preventing yield losses and promoting kernel development. Any method for inactivating the invertase inhibitor in a plant is encompassed by the invention. For example, using a TUSC-like approach, an insertion may be made into the invertase inhibitor coding sequence to disable the gene. See, Benson et al. (1995) *Plant Cell* 7:75–84; Mena et al. (1996) *Science* 274:1537–1540; and U.S. Pat. No. 5,962,764; herein incorporated by reference. Likewise, the coding sequence or antisense sequence for the invertase inhibitor coding sequence may be used to co-suppress or antisense the activity of the invertase inhibitor gene.

Figure 1:
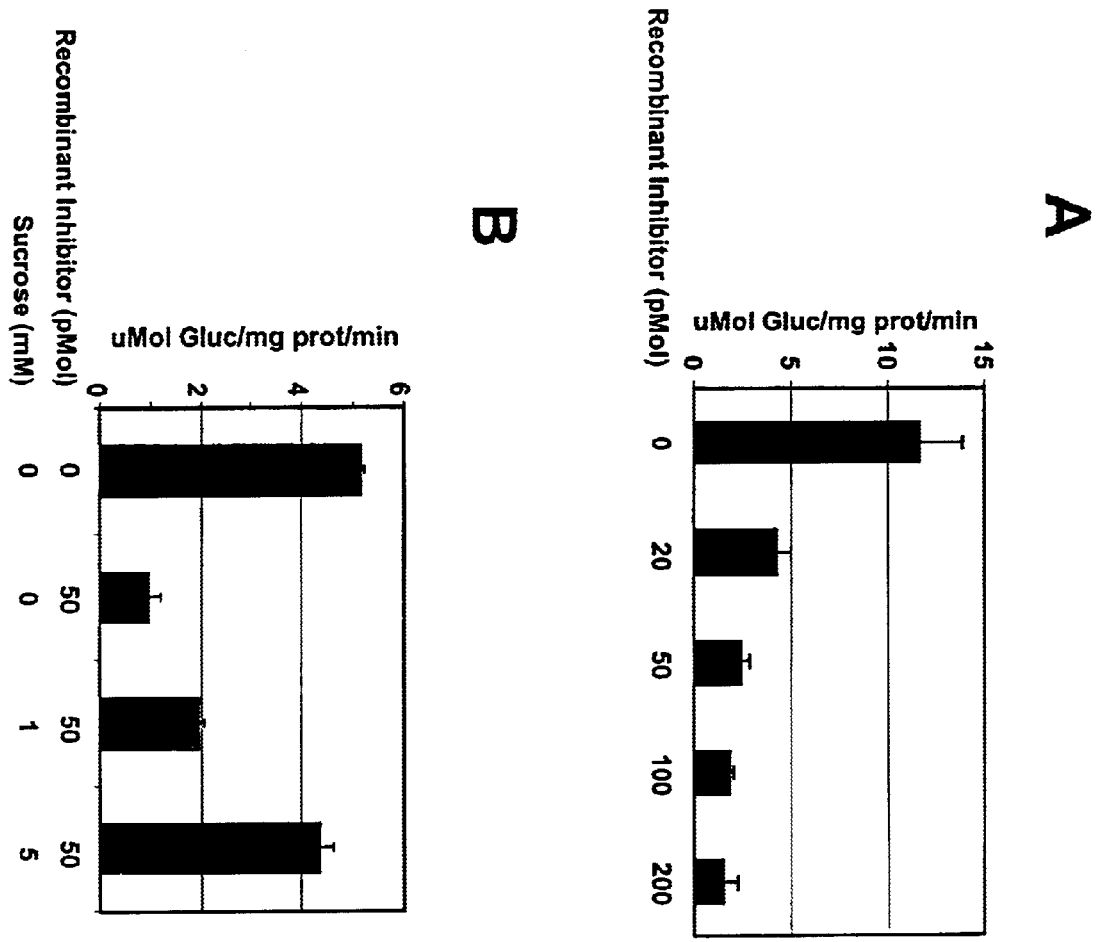
FIG. 1 depicts the effect of recombinant inhibitor on maize invertase activity.
Figure 2:
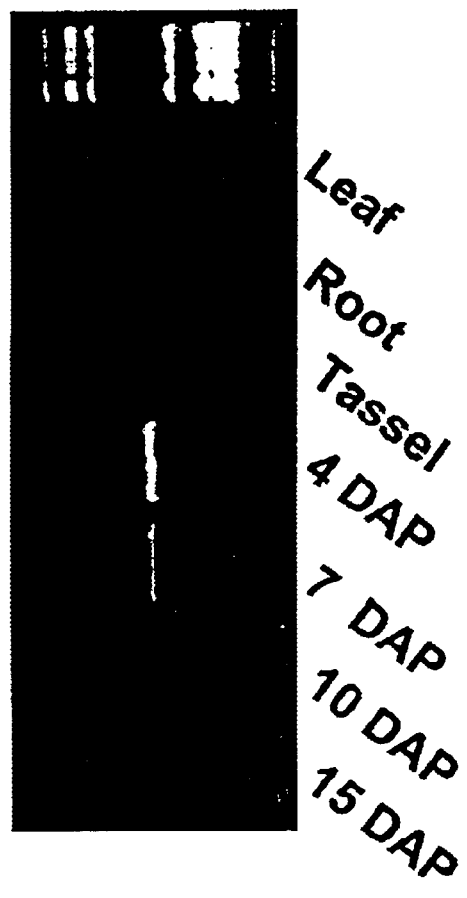
FIG. 2 indicates that gene expression for maize invertase inhibitor is limited to early seed development. RT-PCR was used to detect invertase inhibitor expression in leaf, root, tassel and 4 DAP, 7 DAP, 10 DAP and 15 DAP kernels. Tubulin mRNA was detected as a constitutive control (data not shown).
Figure 3:
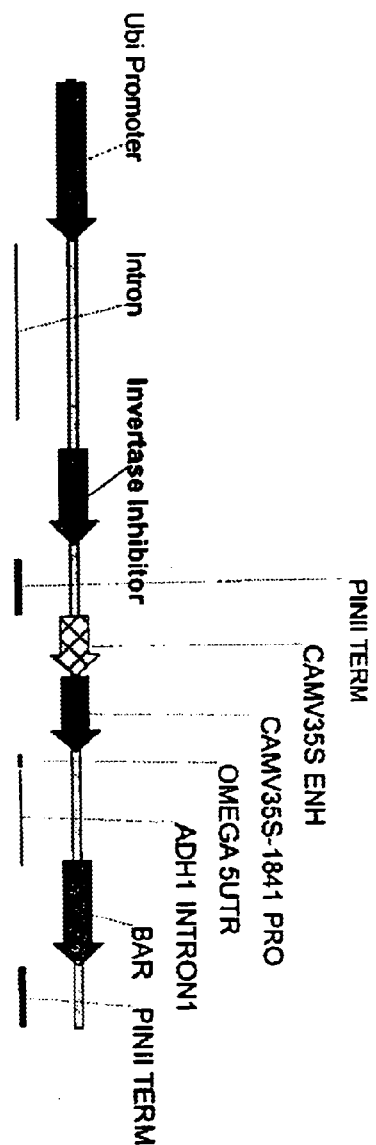
FIG. 3 is a schematic of the transgene construct transferred into maize and arabidopsis plants. The constitutive Ubi (ubiquitin) promoter controls expression of the invertase inhibitor nucleotide sequence.
Figure 4:
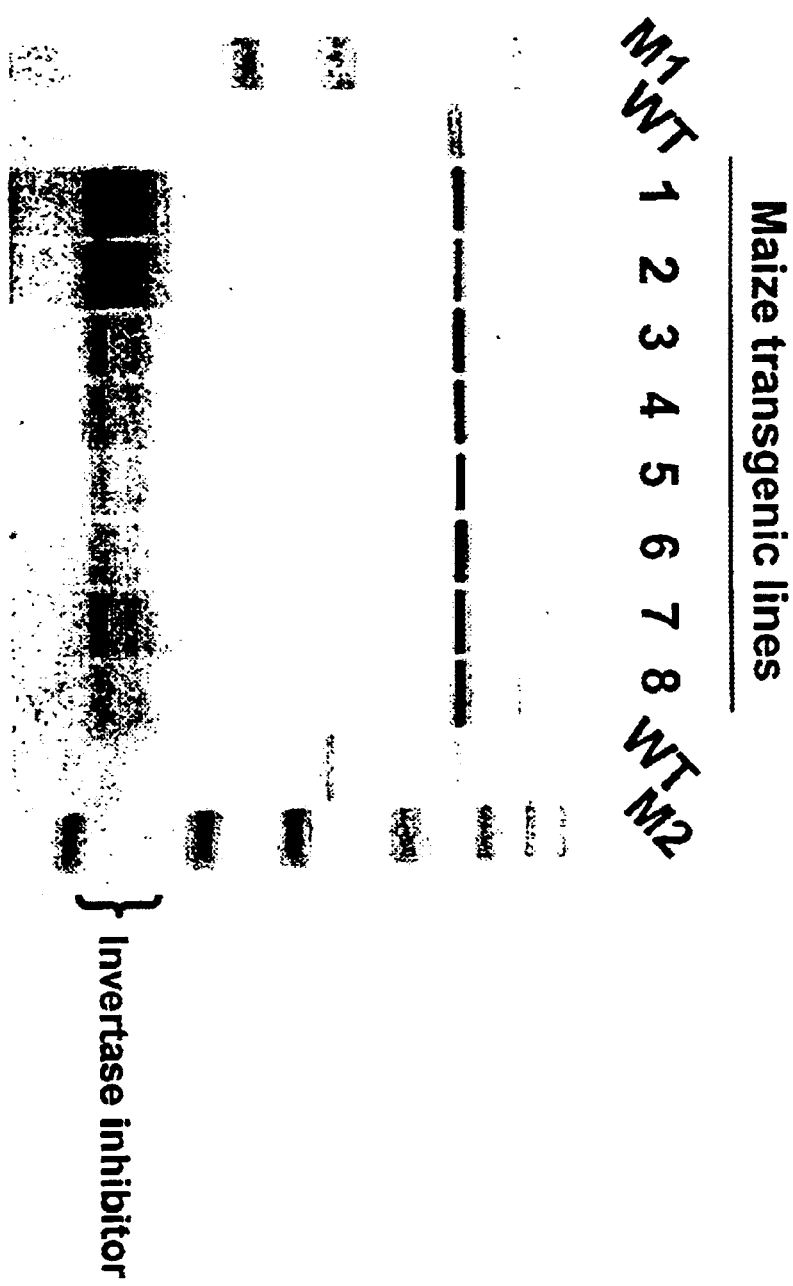
FIG. 4 shows an analysis of overexpression of maize invertase inhibitor in leaf tissue of stable transgenic lines. M1 and M2 are molecular weight markers, while WT present results from an untransformed control.

Unlike previously characterized invertase inhibitors (e.g. WO 98/04722, WO 00/09719), it has been shown that the yeast invertase gene is sensitive to the invertase inhibitors of the invention (Table 1). The yeast invertase is less sensitive to the invertase inhibitors of the invention than other invertases (FIG. 1, Table 1). Therefore the yeast invertase is an attractive option to supplement invertase activity in a plant. The yeast invertase gene could be used in an expression cassette, particularly with promoters to drive expression during early kernel development. Yeast invertase sequences for use in the invention include, for example, Weber et al. (1998) Plant J. 16:163; Sonnewald et al. (1991) Plant J. 1:95–106; von Schaewen et al. (1990) EMBO J. 10: 3033; Silveira et al. (1996) Anal Biochem 238:26, Roitsch et al. (1989) Eur. J. Biochem 181:733; Tussig et al. (1983) Nucleic Acids Res. 11:1943–54; the disclosures of which are herein incorporated by reference. The construct may further comprise an apoplastic targeting signal to direct it to the cell wall. This approach would essentially supplement invertase activity in a plant.

TABLE 1

Effect of recombinant invertase inhibitor on invertase activity. Effect of recombinant invertase inhibitor on invertase activity (umol reducing sugar/mg protein/min; SD in parentheses; n = 3). Yeast values are expressed in mol reducing sugar; n = 6). +Inh = 75 pMol recombinant invertase inhibitor, +Suc = 5 mM sucrose.

| Protein Preparation | Invertase Activity | | |
|---|---|---|---|
| | −Inh, −Suc | +Inh, −Suc | +Inh, +Suc |
| Arabidopsis Soluble | 2.9 (0.11) | 1.6 (0.23) | 2.3 (0.04) |
| Arabidopsis Insoluble | 1.8 (0.09) | 1.3 (0.10) | 1.5 (0.11) |
| Tomato Soluble | 303.8 (8.3) | 248.9 (11.9) | 317.5 (32.7) |
| Tomato Insoluble | 29.2 (5.1) | 12.8 (3.3) | 20.9 (0.44) |
| Yeast | 2.9 (0.20) | 1.7 (0.19) | 1.8 (0.19) |

Compositions of the invention include nucleotide sequences that are involved in invertase inhibitor activity. In particular, the present invention provides for isolated nucleic acid molecules set forth in SEQ ID NO[s]: 1, 4, 7, 10, 13, 16, 19, 22, 25, 28, 31, 34, 37, 40, 43, 46, 49, and 52 comprising nucleotide sequences encoding the amino acid sequences shown in SEQ ID NO[s]: 2, 5, 8, 11, 14, 17, 20, 23, 26, 29, 32, 35, 38, 41, 44, 47, 50, and 53, respectively. The coding sequence of SEQ ID NO[s]: 2, 5, 8, 11, 14, 17, 20, 23, 26, 29, 32, 35, 38, 41, 44, 47, 50, and 53 are provided in SEQ ID NO: 3, 6, 9, 12, 15, 18, 21, 24, 27, 30, 33, 36, 39, 42, 45, 48, 51, and 54, respectively. Further provided are polypeptides having an amino acid sequence encoded by a nucleic acid molecule described herein, for example those set forth in SEQ ID NO[s]: 1, 4, 7, 10, 13, 16, 19, 22, 25, 28, 31, 34, 37, 40, 43, 46, 49, 52, and fragments and variants thereof.

It is recognized that with these nucleotide sequences, antisense constructions, complementary to at least a portion of the messenger RNA (mRNA) for the invertase inhibitor sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably 91%, 92%, 93%, 94%, 95%, 96%, 97%, 98% or 99% sequence identity. See, U.S. Pat. Nos. 5,283,184 and 5,034,323; herein incorporated by reference.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence exhibit invertase inhibitor activity. Alternatively, fragments of a nucleotide sequence that are useful as hybridization probes generally do not encode fragment proteins retaining biological activity. Thus, nucleic acid molecules that are fragments of an invertase inhibitor nucleotide sequence comprise at least 15, 20, 50, 75, 100, 325, 350, 375, 400, 425, 450, 500, 550, 600 or up to 609 nucleotides present in the nucleotide sequences disclosed herein (e.g. 665, 981, 779, 633, 844, 775, 686, 709, 1067, 1214, 782, 814, 766, 826, 983, 609, 673, or 665 nucleotides for SEQ ID NO: 1, 4, 7, 10, 13, 16, 19, 22, 25, 28, 31, 34, 37, 40, 43, 46, 49, or 52, respectively). Alternatively, a nucleic acid molecule that is a fragment of an invertase inhibitor-like nucleotide sequence of the present invention comprises a nucleotide sequence consisting of nucleotides 1–100, 100–200, 200–300, 300–400, 400–500, 500–600, or up to the full length of each nucleotide sequence disclosed herein.

By "variants" is intended substantially similar sequences. For nucleotide sequences, conservative variants include those sequences that, because of the degeneracy of the genetic code, encode the amino acid sequence of the invertase inhibitor polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a protein of the invention. Generally, variants of a particular nucleotide sequence of the invention will have at least 65% or 70%, generally at least 75%, 80%, 85%, preferably about 90%, 91%, 92%, 93%, 94%, 95%, or more preferably 96%, 97%, 98% or 99% sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, invertase inhibitor activity as described herein. Such variants may result from, for example, genetic polymorphism or from human manipulation. Biologically active variants of the invention will have at least 65% or 70%, generally at least 75%, 80%, 85%, preferably 90%, 91%, 92%, 93%, 94%, 95% or more preferably 96%, 97%, 98% or 99% sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by the ability to inhibit invertase activity. See, for example, Weil et al. (1994) *Planta* 193:438–45, herein incorporated by reference.

Variant nucleotide sequences and proteins also encompass sequences and proteins derived from a mutagenic and recombinogenic procedure such as DNA shuffling. With such a procedure, one or more different invertase inhibitor coding sequences can be manipulated to create a new invertase inhibitor possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the invertase inhibitor gene of the invention and other known invertase inhibitor genes to obtain a new gene coding for a protein with an improved property of interest, such as insensitivity to sucrose deprivation. In addition, all or a portion of the nucleotide sequences of the invention that encode a fragment or variant of an invertase inhibitor polypeptide may be shuffled between other invertase inhibitor sequences of the invention or other known invertase inhibitor sequences. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequence[] set forth herein. Sequences isolated based on their sequence identity to the entire sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

To achieve specific hybridization under a variety of conditions, probes include sequences that are unique among invertase inhibitor sequences and are preferably at least about 10 nucleotides in length, and most preferably at least about 20 nucleotides in length. Such probes may be used to amplify corresponding sequences from a chosen plant or organism by PCR. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m = 81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with $\geq 90\%$ identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an invertase inhibitor protein and which hybridize under stringent conditions to the sequences disclosed herein, or to fragments thereof, are encompassed by the present invention. Such sequences will be at least about 60%, 65%, or 70% homologous, and even at least about 75%, 80%, 85%, 90%, 91%, 92%, 93%, 94%, 95%, 96%, 97%, 98%, 99% or more homologous with the disclosed sequence[s]. That is, the sequence identity of sequences may range, sharing at least about 60%, 65%, or 70%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, 91%, 92%, 93%, 94%, 95%, 96%, 97%, 98%, 99%, or more sequence identity.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 65% or 70% sequence identity to a reference sequence, preferably 80%, more preferably 85%, most preferably at least 90%, 91%, 92%, 93%, 94%, 95%, 96%, 97%, 98%, 99% or more sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The invertase inhibitor sequences of the invention, including coding sequences and antisense sequences, may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the sequence of interest to be under the transcriptional regulation of the regulatory regions. The expression cassette may additionally contain selectable marker genes.

The expression cassette will include in the 5'-3' direction of transcription, a transcriptional and translational initiation region, an invertase inhibitor sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the promoter sequences used to regulate expression of the claimed nucleotide sequences may be used. Such constructs would change expression levels of invertase inhibitors in the plant or other host cell of interest. Thus, the phenotype of the plant cell or the host cell (i.e. plant, plant cell, or organism of interest) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.*

17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y,), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core promoter of the Rsyn7 promoter (WO 99/43838 and U.S. Pat. No. 6,072,050); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase). Gama-zein is one example of endosperm-preferred promoter. Glob-1 is one example of embryo-preferred promoter. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, g-zein, waxy, shrunken 1, shrunken 2, globulin 1, etc.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.*

84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the invertase inhibitor of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The present invention may be used for transformation of any plant species, including, but not limited to, monocots and dicots. Examples of plants of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

The following examples are offered by way of illustration and not by way of limitation.

EXPERIMENTAL

EXAMPLE 1

Transformation and Regeneration of Transgenic Plants

Immature maize embryos from greenhouse donor plants are bombarded with a plasmid containing the antisense sequence corresponding to SEQ ID NO: 1 operably linked to an Ubi promoter plus a plasmid containing the selectable marker gene PAT (Wohlleben et al. (1988) *Gene* 70:25–37) that confers resistance to the herbicide Bialaphos. Transformation is performed as follows. Media recipes follow below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.
Preparation of DNA A plasmid vector comprising the antisense sequence corresponding to SEQ ID NO: 1 operably linked to a Rsgn7 promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.
Particle Gun Treatment The sample plates are bombarded at level #4 in particle gun #HE34-1 or #HE34-2. All samples receive a single shot at 650 PSI, with a total of ten aliquots taken from each tube of prepared particles/DNA.
Subsequent Treatment Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored.
Bombardment and Culture Media Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 2

Agrobacterium-mediated Transformation

For Agrobacterium-mediated transformation of maize with a nucleotide sequence of the invention, preferably the method of Zhao is employed (PCT patent publication WO98/32326), the contents of which are hereby incorporated by reference. Briefly, immature embryos are isolated from maize and the embryos contacted with a suspension of Agrobacterium, where the bacteria are capable of transferring the sequences of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 3

Soybean Embryo Transformation

Soybean embryos are bombarded with a plasmid containing the invertase inhibitor gene operably linked to a promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) Nature (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188), and the 3' region of the nopaline synthase gene from the T-DNA of the Ti plasmid of Agrobacterium tumefaciens. The expression cassette comprising the invertase inhibitor gene operably linked to a preferred promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   a) the nucleotide sequence set forth in SEQ ID NO:1;
   b) a nucleotide sequence having at least 95% sequence identity to the sequence set forth in SEQ ID NO:1, wherein said nucleotide sequence encodes a polypeptide having invertase inhibitor activity; and
   c) a nucleotide sequence that is a complement of a) or b).

2. The nucleic acid molecule of claim 1, wherein said sequence encodes an amino acid selected from the group consisting of:
   a) the amino acid sequence set forth in SEQ ID NO:2[[.]]; and
   b) an amino sequence having 95% sequence identity to the sequence set forth in SEQ ID NO:2.

3. A chimeric gene comprising a plant-functional promoter operably linked to the nucleotide sequence of claim 1.

4. The chimeric gene of claim 3, wherein the nucleotide sequence encodes the amino acid sequence set forth in SEQ ID NO:2.

5. The chimeric gene of claim 3, wherein the nucleotide sequence is the sequence set forth in SEQ ID NO:1.

6. The chimeric gene of claim 3, wherein said nucleotide sequence is an antisense sequence of the sequence set forth in SEQ ID NO:1.

7. A vector comprising the chimeric gene of claim 3.

8. A plant cell transformed with the chimeric gene of claim 3.

9. A plant comprising the chimeric gene of claim 3.

10. A transformed plant having incorporated into its genome a DNA molecule, said molecule comprising a nucleotide sequence operably linked to a promoter capable of driving expression of a gene in a plant cell, wherein said nucleotide sequence is selected from the group consisting of:
    a) a sequence encoding the amino acid sequence set forth in SEQ ID NO:2;
    b) the nucleotide sequence set forth in SEQ ID NO:1;
    c) a nucleotide sequence having at least 95% sequence identity to the sequence set forth in SEQ ID NO:1, wherein said nucleotide sequence encodes a polypeptide having invertase inhibitor activity;
    d) a nucleotide sequence that encodes an amino acid sequence having 95% sequence identity to the sequence of SEQ ID NO:2; and
    e) nucleotide sequence that is a complement of any one of a)–d).

11. The transformed plant of claim 10, wherein the nucleotide sequence is the nucleotide sequence set forth in SEQ ID NO:2.

12. The transformed plant of claim 11, wherein the nucleotide sequence is the nucleotide sequence set forth in SEQ ID NO:1.

13. The transformed plant of claim 10, wherein said plant is a dicot.

14. The transformed plant of claim 10, wherein said plant is a monocot.

15. The transformed plant of claim 14, wherein said plant is maize.

16. Transformed seed of the plant of any one of claims 13–15.

17. A method for modulating invertase activity in a plant, said method comprising transforming said plant with a DNA construct, said construct comprising a promoter that drives expression in a plant cell operably linked with a nucleotide sequence selected from the group consisting of:
    a) a sequence encoding the amino acid sequence set forth in SEQ ID NO:2;
    b) the nucleotide sequence set forth in SEQ ID NO:1;
    c) a nucleotide sequence having at least 95% sequence identity to the sequence set forth in SEQ ID NO:1, wherein said nucleotide sequence encodes a polypeptide having invertase inhibitor activity;
    d) a nucleotide sequence that encodes an amino acid sequence having 95% sequence identity to the sequence of SEQ ID NO:2; and
    e) nucleotide sequence that is a complement of any one of a)–d).

18. A method for increasing seed yield in a plant, said method comprising transforming said plant with a DNA construct, said construct comprising a promoter that drives expression in a plant cell operably linked with a nucleotide sequence selected from the group consisting of:
    a) a sequence encoding the amino acid sequence set forth in SEQ ID NO:2;
    b) the nucleotide sequence set forth in SEQ ID NO:1;
    c) a nucleotide sequence having at least 95% sequence identity to the sequence set forth in SEQ ID NO:1, wherein said nucleotide sequence encodes a polypeptide having invertase inhibitor activity;
    d) a nucleotide sequence that encodes an amino acid sequence having 95% sequence identity to the sequence of SEQ ID NO:2; and
    e) nucleotide sequence that is a complement of any one of a)–d).

19. A transformed plant cell having incorporated into its genome a DNA molecule, said molecule comprising a promoter capable of driving expression of a gene in a plant cell operably linked to a nucleotide sequence selected from the group consisting of:
    a) a sequence encoding the amino acid sequence set forth in SEQ ID NO:2;
    b) the nucleotide sequence set forth in SEQ ID NO:1;
    c) a nucleotide sequence having at least 95% sequence identity to the sequence set forth in SEQ ID NO:1, wherein said nucleotide sequence encodes a polypeptide having invertase inhibitor activity;
    d) a nucleotide sequence that encodes an amino acid sequence having 95% identity to the sequence of SEQ ID NO:2; and
    e) nucleotide sequence that is a complement of any one of a)–d).

* * * * *

UNITED STATES PATENT AND TRADEMARK OFFICE
CERTIFICATE OF CORRECTION

PATENT NO.     : 6,713,666 B2
DATED          : March 30, 2004
INVENTOR(S)    : Helentjaris et al.

It is certified that error appears in the above-identified patent and that said Letters Patent is hereby corrected as shown below:

Column 85,
Lines 59 and 60, "is the nucleotide sequence set forth in SEQ ID NO:2" should read
-- encodes the amino acid sequence set forth in SEQ ID NO:2 --;
Line 61, "claim 11" should read -- claim 10 --.

Column 86,
Line 62, "95% identity" should read -- 95% sequence identity --.

Signed and Sealed this

Thirtieth Day of November, 2004

JON W. DUDAS
*Director of the United States Patent and Trademark Office*